US010132806B2

(12) United States Patent
Marotta

(10) Patent No.: US 10,132,806 B2
(45) Date of Patent: Nov. 20, 2018

(54) ANTIGENS DERIVED FROM CITRULLINATED 14-3-3 AND USES THEREOF IN THE DIAGNOSIS OF RHEUMATOID ARTHRITIS

(71) Applicant: Augurex Life Sciences Corporation, North Vancouver (CA)

(72) Inventor: Anthony Marotta, Burnaby (CA)

(73) Assignee: AUGUREX LIFE SCIENCES CORP., Vancouver, British Columbia ( * ) Notice: Subject to any disclaimer, the term of this patent is extended or adjusted under 35 U.S.C. 154(b) by 117 days.

(21) Appl. No.: 14/353,281

(22) PCT Filed: Oct. 19, 2012

(86) PCT No.: PCT/CA2012/050748
§ 371 (c)(1),
(2) Date: Apr. 21, 2014

(87) PCT Pub. No.: WO2013/056377
PCT Pub. Date: Apr. 25, 2013

(65) Prior Publication Data
US 2014/0255957 A1 Sep. 11, 2014

Related U.S. Application Data

(60) Provisional application No. 61/550,046, filed on Oct. 21, 2011.

(51) Int. Cl.
*G01N 33/564* (2006.01)
*G01N 33/543* (2006.01)
*C07K 14/47* (2006.01)
*G01N 33/68* (2006.01)

(52) U.S. Cl.
CPC .......... *G01N 33/564* (2013.01); *C07K 14/47* (2013.01); *C07K 14/4713* (2013.01); *G01N 33/54306* (2013.01); *G01N 33/6893* (2013.01); *G01N 2440/18* (2013.01); *G01N 2800/105* (2013.01)

(58) Field of Classification Search
None
See application file for complete search history.

(56) References Cited

U.S. PATENT DOCUMENTS

| | | | |
|---|---|---|---|
| 4,956,281 A | 9/1990 | Wallner et al. |
| 5,948,765 A | 9/1999 | Shaw et al. |
| 5,976,852 A | 11/1999 | Cheng et al. |
| 5,998,149 A | 12/1999 | Hsieh et al. |
| 6,596,476 B1 | 7/2003 | Lesniewski et al. |
| 7,011,952 B2 | 3/2006 | Hageman et al. |
| 7,056,677 B2 | 6/2006 | Takahasi et al. |
| 7,101,962 B2 | 9/2006 | Burke et al. |
| 7,171,311 B2 | 1/2007 | Dai et al. |
| 7,396,654 B2 | 7/2008 | Hayes et al. |
| 7,919,262 B2 | 4/2011 | Yacoubian et al. |
| 7,939,272 B2 | 5/2011 | Buck |
| 2003/0119054 A1 | 6/2003 | Mrksich et al. |
| 2004/0152630 A1 | 8/2004 | Fu et al. |
| 2005/0009094 A1 | 1/2005 | Mueller |
| 2005/0042681 A1 | 2/2005 | Van Eyk et al. |
| 2008/0220013 A1 | 9/2008 | Hochstrasser et al. |
| 2009/0093005 A1 | 4/2009 | Smalley et al. |
| 2010/0016173 A1 | 1/2010 | Nagalla et al. |
| 2011/0052573 A1 | 3/2011 | Marotta |
| 2012/0077695 A1 | 3/2012 | Ostroff et al. |
| 2012/0101002 A1 | 4/2012 | Riel-Mehan et al. |

FOREIGN PATENT DOCUMENTS

| | | |
|---|---|---|
| JP | 2005-181342 A | 7/2005 |
| WO | WO 1997/33601 A1 | 9/1997 |
| WO | WO 1997/38315 A1 | 10/1997 |
| WO | WO 1998/026293 A1 | 6/1998 |
| WO | WO 1999/046401 A2 | 9/1999 |
| WO | WO 2003/071927 A2 | 9/2003 |
| WO | WO 2005/053811 A2 | 6/2005 |
| WO | WO 2005/120568 A1 | 12/2005 |
| WO | WO 2006/126008 A2 | 11/2006 |
| WO | WO 2007/095250 A2 * | 8/2007 |
| WO | WO 2007/128132 A1 | 11/2007 |
| WO | WO 2009/067811 A1 | 6/2009 |
| WO | WO2009067820 A1 * | 6/2009 |
| WO | WO 2009/137832 A2 | 11/2009 |
| WO | WO2010102412 A1 * | 9/2010 |

OTHER PUBLICATIONS

Kuhn et al. "Antibodies against citrullinated proteins enhance tissue injury in experimental autoimmune arthritis", J. Clin. Invest. 116:961-973 (2006). doi:10.1172/JCI25422.*
Girbal-Neuhauser et al. "The Epitopes Targeted by the Rheumatoid Arthritis-Associated Antifilaggrin Autoantibodies are Posttranslationally Generated on Various Sites of (Pro)Filaggrin by Deimination of Arginine Residues", J Immunol Jan. 1, 1999, 162 (1) 585-594 (Year: 1999).*
Corconnier et al., "Diagnostic value of anti-RA33 antibody, antikeratin antibody, antiperinuclear factor and antinuclear antibody in early rheumatoid arthritis: comparison with rheumatoid factor," Br. J. Rheumatol., vol. 35, pp. 620-624 (1996).
Gabay et al., "Occurrence of antiperinuclear, antikeratin, and anti-RA 33 antibodies in juvenile chronic arthritis," Ann. Rheum. Dis., vol. 52, pp. 785-789 (1993).
Kilani et al., "Detection of high levels of 2 specific isoforms of 14-3-3 proteins in synovial fluid fom patients with joint inflamation," J. Rheum., vol. 34(8), pp. 1650-1657 (2007).
Kim et al., "When does rheumatoid arthritis begin and why do we need to know?" Athritis. Reheum., vol. 43, pp. 473-484 (2000).
Knuckley et al., "Substrate Specificity and Kinetic Studies of PADs 1, 3, and 4 Identify Potent and Selective Inhibitors of Protein Arginine Deiminase 3," Biochem., vol. 49, pp. 4852-4863 (2010).

(Continued)

*Primary Examiner* — Christine Foster
(74) *Attorney, Agent, or Firm* — Todd A. Lorenz

(57) ABSTRACT

The present invention provides citrullinated 14-3-3η peptides and antibodies thereto and methods of using same to evaluate arthritic conditions such as rheumatoid arthritis.

6 Claims, 2 Drawing Sheets
Specification includes a Sequence Listing.

(56) References Cited

OTHER PUBLICATIONS

Maksymowych et al., "14-3-3 Eta is a novel citrullination target in rheumatoid arthritis that enhances diagnostic utility in anti-CCP negative patients," Arth. Rheum., vol. 64(10S), pp. S423-S424 (2012).
Meyer et al., "Anticirullinated protein/peptide antibody assays in early rheumatoid arthritis for preceding five year radiographic damage," Ann. Rheum. Dis., vol. 62(2), pp. 120-126 (2003).
Nakayama-Hamada et al., "Comparison of enzymatic properties between hPADI2 and hPADI4," Biochemical and Biophysical Research, vol. 327, pp. 192-200 (2005).
van Venrooij, Walter J. and Pruijn, Ger J. M., "Citrullination: a small change for a protein with great consequences for rheumatoid arthritis," Arthritis Res., vol. 52, pp. 785-789 (2000).
Vincent et al. "High diagnostic value in rheuMatoid arthritis of antibodies to the stratum corneum of rat oesophagus epithelium, so-called 'antikeratin antibodies'" Ann. Rheum. Dis., vol. 48, pp. 712-722 (1989).
Qiu et al., "Occurrence of autoantibodies to annexin I, 14-3-3 theta and LAMR1 in prediagnostic lung cancer sera." Journal of Clinical Oncology, vol. 26, No. 31, pp. 5060-5066 (2008).
Ahrens, D. et al., "Expression of matrix metalloproteinase 9 (96-kd gelatinase B) in human arthritis," Arthritis & Rheum. vol. 39, pp. 1576-1587 (1996).
Ausubel, F. et al., "Current Protocols in Molecular Biology", Ch. 1 Immunoassays, pp. 11.0.1-11.3.6, John Wiley & Sons, New York (1998).
Ausubel, F. et al., "Short Protocols in Molecular Biology", Ch. 11 Immunology, pp. 11-4-11-5, John Wiley & Sons, New York (2008).
Bombara, MP et al., "Cell contact between T cells and synovial fibroblasts causes induction of adhesion molecules and cytokines," J. Leukocyte Biol. vol. 54, pp. 339-406 (1993).
Boston, P. et al., "Human 14-3-3 Protein:Radioimmunoassay, Tissue Distribution, and Cerebrospinal Fluid Levels in Patients With Neurological Disorders,"J. N. Chem. vol. 38, pp. 1475-1482 (1982).
Brand, DD., "Rodent models of rheumatoid arthritis," Comp. Med., vol. 55(2), pp. 114-122 (2005).
Burger, D. et al., "Imbalance between interstitial collagenase and tissue inhibitor of metalloproteinases 1 in synoviocytes and fibroblasts upon direct contact with stimulated T lymphocytes: involvement of membrane-associated cytokines," Arthritis Rheum., vol. 41(10), pp. 1748-1759 (1998).
Chan, TA et al., "14-3-3Sigma is required to prevent mitotic catastrophe after DNA damage," Nature, vol. 401, pp. 616-620 (1999).
Cho, ML et al., "Effector function of type II collagen-stimulated T cells from rheumatoid arthritis patients: cross-talk between T cells and synovial fibroblasts," Arthritis Rheum., vol. 50(3), pp. 776-784 (2004).
Craparo, A. et al., "14-3-3 (ε) Interacts with the insulin-like growth factor I receptor and insulin receptor substrate I in a phosphoserine-dependent manner," J. Biol. Chem., vol. 272(17), pp. 11663-11669 (1997).
Daien, Claire I. and Morel, Jacques, "Predictive Factors of Response to Biological Disease Modifying Antirheumatic Drugs: Towards Personalized Medicine," Mediators of Inflammation, vol. 2014: 386148, pp. 1-11 (2014).
Da Silva et al., "Safety of low dose glucocorticoid treatment in rheumatoid arthritis: published evidence and prospective trial data," Ann. Rheum Dis., vol. 65, pp. 285-293 (2006).
Di Fede, G. et al., "The ε isoform of 14-3-3 protein is a component of the prion protein amyloid deposits of Gerstmann-Straussler-Scheinker Disease," J. Neuropathology and Experimental Neurology, vol. 66(2), pp. 124-130 (2007).
Du et al., "Association of a phospholipase A2 (14-3-3 protein) with the platelet glycoprotein Ib-IX Complex," J. Biol. Chem., vol. 269(28), pp. 18287-18290.

Firestein, Gary S.,"Rheumatoid Arthritis: Rheumatoid Synovitis and Pannus," Rheumatology, pp. 5/13.1-5/13.5, Mosby, London (1997).
Frank, R. et al., "Spot synthesis: An easy technique for the positionally addressable, parallel chemical synthesis on a membrane support," Tetrahedron, vol. 48, pp. 9217-9232 (1992).
Fu, H. et al., "14-3-3 proteins: structure, function and regulation," Annul. Rev. Pharmacol. Toxicol., vol. 40, pp. 617-647 (2000).
Furst et al., "Consensus Statement: Updated consensus statement on biological agents, specifically tumour necrosis factor α (TNFα) blocking agents and interleukin-1 receptor antagonist (IL-1ra), for the treatment of rheumatic diseases, 2005" Ann. Rheum Dis., vol. 64, pp. iv2-iv14 (2005).
Ghahary, A, et al., "Keratinocyte-releasable stratifin functions as a potent collagenase-stimulating factor in fibroblasts," J. Invest. Dermatol., vol. 122, pp. 1188-1197 (2004).
Gilbert M. R., "Neurological Complications" in Abeloff MD et al., Clinical Oncology, 3rd Ed., pp. 1213-1246, Churchill Livingstone/Elsevier Press, New York (2004).
Goldstein et al., "Selective p38α Inhibitors Clinically Evaluated for the Treatment of Chronic Inflammatory Disorders," J. Med. Chem., vol. 53, pp. 2345-2353 (2010).
Harris E D Jr., "Cytokines, Lymphokines, Growth Factors, and Chemokines," In: Rheumatoid Arthritis. Philadelphia: W.B. Saunders Company, pp. 105-125 (1997).
Harris E D Jr., "History and Epidemiology of Rheumatoid Arthritis: How long has it affected us, and who is at risk?," In: Rheumatoid Arthritis. Philadelphia: W.B. Saunders Company, pp. 121-127 (1997).
Harris E D Jr., "Introduction," In: Rheumatoid Arthritis. Philadelphia: W.B. Saunders Company, pp. xix-xxiii (1997).
Harris E D Jr., "Rheumatoid Synovium: Complex, and More Than the Sum of its Parts. In: Rheumatoid Arthritis," Philadelphia: W.B. Saunders Company, pp. 126-149, (1997).
Harlow, E., and Lane, D., "Antibodies: A Laboratory Manual," pp. 553-612, Cold Spring Harbor Laboratory Press, Cold Spring Harbor (1988).
Harlow, E. and Lane, D., "Antibodies: A Laboratory Manual," Cold Spring Harbor Laboratory Press, Cold Spring Harbor, NY, pp. 23-26 (1988).
Hermeking, H. et al., "14-3-3σ is a p53-regulated inhibitor of G2/M progression," Molecular Cell, vol. 1, pp. 3-11 (1997).
Hopp, Thomas P. and Woods, Kennith, R. et al., "Prediction of protein antigenic determinants from amino acid sequences," Proc. Natl. Acad. Sci. USA., vol. 78, No. 6, pp. 3824-3828 (1981).
Hsich, G, et al., "The 14-3-3 brain protein in cerebrospinal fluid as a marker for transmissible spongiform encephalopathies," N. Engl. J. Med. , vol. 335, pp. 924-930 (1996).
"14-3-3 eta Antibody (6A12): sc-293464" https://www.scbt.com/scbt/product/14-3-3-eta-antibody-6a12, downloaded Apr. 17, 2017, (4 pages total).
Ichimura, T. et al., "Brain 14-3-3 protein is an activator protein that activates tryptophan 5-monooxynease in the presence of $Ca^{2+}$, calmodulin-dependent protein kinase II," FEBS Lett., vol. 219, pp. 79-82 (1987).
Ichimura, T. et al., "Molecular cloning of cDNA coding for brain-specific 14-3-3 protein, a protein kinase-dependent activator of tyrosine and tryptophan hydroxylases," Proc. Natl. Acad. Sci. USA, vol. 85, pp. 7084-7088 (1988).
Jamal et al., "Increased expression of human type IIa secretory phospholipase A2 antigen in arthritic synovium," Ann. Rheum. Dis., vol. 57, pp. 550-558 (1998).
JaMBW Chapter 3.1.7, Antigenicity Plot (employing Hopp and Woods method), (http://www.bioinformatics.org/JaMBW/3/1/7/), pp. 1-2, printed Sep. 26, 2012.
Jasser, MZ et al., "Induction of stromelysin-1 and collagenase synthesis in fibrochondrocytes by tumor necrosis factor-alpha," Matrix Biology vol. 14, p. 241 (1994).
Jiang, J. et al., "Multifunctional proteins bridge mitosis with motility and cancer with inflammation and arthritis," The Scientific World Journal, vol. 10, pp. 1244-1257 (2010).
Kandpal et al., "Expression of Protein Kinase Regulator Genes in Human Ear and Cloning of a Gamma Subtype of the 14-3-3 Family of Proteins," DNA and Cell Biology, vol. 16(4), pp. 455-462 (1997).

(56) References Cited

OTHER PUBLICATIONS

Katrib, A. et al., "What can we learn from the synovium in early rheumatoid arthritis?," Inflamm. Res. vol. 51, pp. 170-175 (2002).
Katz, A. B. et al., "A Partial Catalog of Proteins Secreted by Epidermal Keratinocytes in Culture," J. Invest. Dermatol., vol. 112, pp. 818-821 (1999).
Kim et al., "Role of the 14-3-3η as a Positive Regulator of the Glucocorticoid Receptor Transcriptional Activation," Endocrinology, vol. 146(7), pp. 3133-3140 (2005).
Kohler et al., "Continuous cultures of fused cells secreting antibody of predefined specificity," Nature, vol. 256, pp. 495-497 (1975).
Konttinen et al., "New collagenolytic enzymes identified at the pannus-hard tissue junction in rheumatoid arthritis: destruction from above," Matrix Biol. Vo. 17(8-9), pp. 585-601 (1998).
Konttinen et al., "Analysis of 16 Different Matrix Metalloproteinases (MMP-1 to MMP-20) in the Synovial Membrane: different profiles in trauma and rheumatoid arthritis," Ann. Rheum. Dis., vol. 58, pp. 691-697 (1999).
Krensky et al., "Immunomodulators: Immunosuppressive Agents, Tolerogens, and Immunostimulants," in Hardman—10th Ed., pp. 1461-1483, McGraw Hill, New York (2001).
Laronga, C. et al., "Association of the cyclin-dependent kinases and 14-3-3 sigma negatively regulates cell cycle progression," J. Biol. Chem., vol. 275(30), pp. 23016-23112 (2000).
Leite, John—Invitrogen Corporation, Carlsbad, CA, USA, "Protein detection by Mass Spectrometry," www.invitrogen.com/piq., downloaded Jan. 4, 2013.
Lindy, O. et al., "Matrix metalloproteinase 13 (collagenase 3) in human rheumatoid synovium," Arthritis Rheum., vol. 40(8), pp. 1391-1399 (1997).
Lipsky, Peter E., "Rheumatoid Arthritis", in Braunwald—Harrison's Principles of Internal Medicine, 15th Ed., pp. 1928-1937, McGraw Hill, New York (2001).
Lyons et al., "Effective Use of Autoantibody Tests in the Diagnosis of Systemic Autoimmune Disease," Ann. N.Y. Acad. Sci., vol. 1050, pp. 217-228 (2005).
Ma et al., "Enhanced production of mouse hybridomas to picomoles of antigen using EL-4 conditioned media with an in vitro immunization protocol," In Vitro, vol. 20(9), p. 739-742 (1984).
Maksymowych et al., "14-3-3: A rheumatoid arthritis biomarker," Arthritis and Rheumatism, Vo. 63, No. 10, Suppl. 1. Abstract No. 358 (2011).
Maksymowych et al., "Autoantibody to 14-3-3 ETA Is a Novel Biomarker Associated With MRI Inflammation and Radiographic Progression in Axial Spondyloarthritis," Ninth International Congress on Spondyloarthritis, Clinical and Experimental Rheumatology, vol. 32, pp. 765-838 (2014).
Maksymowych et al., "14-3-3η Autoantibodies: Diagnostic Use in Early Rheumatoid Arthritis," The Journal of Rheumatology, vol. 42, pp. 1-9 (2015).
Martin et al., "Antibodies against the major brain isoforms of 14-3-3 protein. An antibody specific for the N-acetylated amino-terminus of a protein," FEBS Letters, vol. 331(3), pp. 296-303 (1993).
Martin et al., "Subcellular Localisation of 14-3-3 Isoforms in Rat Brain Using Specific Antibodies," J. of Neurochemistry, vol. 63, pp. 2259-2265 (1994).
McInnes et al., "Cell-cell interactions in synovitis interactions between T lymphocytes and synovial cells," Arthritis Research, vol. 2(5), pp. 374-378 (2000).
Megidish et al., "A Novel Sphingosine-dependent Protein Kinas (SDK1) Specifically Phosphorylates Certain Isoforms of 14-3-3 Protein," J. Biol. Chem. vol. 273, No. 34, pp. 21834-21845 (1998).
Miranda-Carús, et al., "IL-15 and the initiation of cell contact-dependent synovial fibroblast-T lymphocyte cross-talk in rheumatoid arthritis: effect of methotrexate," J. Immunol., vol. 173, pp. 1463-1476 (2004).
Molina et al., "Improved Performances of Spot Multiple Peptide Synthesis," Journal of Peptide Application, Synthesis and Analysis, vol. 9, No. 3, pp. 151-155 (1996).

Moore et al., "Nutrition and Lysosomal Activity. The influence of vitamin E deficiency and its duration on the stability of lysosomes in the kidneys of rats," Biochem. J., vol. 103, pp. 923-928 (1967).
Moore et al., "Specific Acidic Proteins of the Nervous System", in Carson FD, pp. 343-359 (1967).
Moreira et al., "A Combined Proteome and Ultrastructural Localization Analysis of 14-3-3 Proteins in Transformed Human Amnion (AMA) Cells," Molecular & Cellular Proteomics, vol. 7, pp. 1225-1240 (2008).
Neeck et al., "Involvement of the glucocorticoid receptor in the pathogenesis of rheumatoid arthritis," Ann. New York Academy of Sciences, vol. 966, pp. 491-495 (2002).
Plotz, "The autoantibody repertoire: searching for order," Nat. Immunol. Rev., vol. 3, pp. 73-78 (2003).
Poole, A. R., "Cartilage in Health and Disease," in Koopman WJ—Arthritis and Allied Conditions, 14th Ed., pp. 226-284, Williams & Wilkins, Baltimore (2001).
R&D Systems 2007, "Affinity-Purified Goat Anti-human/mouse/rat 14-3-3 eta Antibody," Catlog No. AF4420 (2007), (one page).
Roman-Blas, J. A. and Jimenez, S. A., "NF-κB as a potential therapeutic target in osteoarthritis and rheumatoid arthritis," Osteoarthritis and Cartilage, vol. 14, pp. 839-848 (2006).
Rosenau et al., "Autoantibodies to Tumor Necrosis Factor in Patients with Rheumatoid Arthritis and Systemic Lupus Erythematosus," J Rheumatol vol. 36, pp. 753-756 (2009).
Sakaguchi et al., "Animal models of arthritis caused by systemic alteration of the immune system," Curr. Opin. Immunol., vol. 17(6), pp. 589-594 (2005).
Sambrook, J., "Molecular Cloning—Protein Interaction Technologies—A Laboratory Manual," pp. 655-688, Cold Spring Harbor Laboratory Press (2001).
Santa Cruz Biotech, "14-3-3 eta Antibodies," downloaded Mar. 31, 2015 from www.scbt.com, (2 pages total).
Sato et al., "14-3-3η is a novel regulator of parkin ubiquitin ligase," The EMBO Journal, vol. 25, pp. 211-221 (2006).
Satoh et al., "The 14-3-3 protein ε isoform expressed in reactive astrocytes in demyelinating lesions of multiple sclerosis binds to vimentin and glial fibrillary acidic protein in culture human astrocytes," Amer. J. of Pathology, vol. 165, pp. 577-592 (2004).
Scheiman, James M and Fendrick, A Mark, "Practical approaches to minimizing gastrointestinal and cardiovascular safety concerns with COX-2 inhibitors and NSAIDs," Arth. Res and Therap. vol. 9, Suppl. 4, pp. S23-S29 (2005).
Sjowall et al., "Beware of Antibodies to Dietary Proteins in "Antigen-specific" Immunoassays! Falsely Positive Anticytokine Antibody Tests Due to Reactivity with Bovine Serum Albumin in Rheumatoid Arthritis (The Swedish TIRA Project)," J Rheumatol, vol. 38, pp. 215-220 (2011).
Skogh et al., "Twenty Eight Joint Count Disease Activity Score in Recent Onset Rheumatoid Arthritis Using C Reactive Protein . . . " Ann. Rheum Dis. vol. 62, pp. 681-682 (2003).
Smeets et al., "The effects of interferon-beta treatment of synovial inflammation and expression of metalloproteinases with rheumatoid arthritis," Arthritis Rheum., vol. 43, No. 2, pp. 270-274 (2000).
Sorsa et al., "Collagenase in synovitis of rheumatoid arthritis," Arthritis Rheum., vol. 22, pp. 44-53 (1992).
Takashashi et al., "Functional interaction of the immunosuppressant mizoribine with the 14-3-3 protein," Biochemical and Biophysical Research Communications, vol. 274, pp. 87-92 (2000).
Tohyama et al., "Localization of human glucocorticoid receptor in rheumatoid synovial tissue of the knee joint," Scandinavian J. Rheum., vol. 34, pp. 426-432 (2005).
Toker et al., "Protein kinase C inhibitor proteins. Purification from sheep brain and sequence similarity to lipocortins and 14-3-3 protein," Eur. J. Biochem., vol. 191(2), pp. 421-429 (1990).
Tolboom et al., "Invasive properties of fibroblast-like synoviocytes: correlation with growth characteristics and expression of MMP-1, MMP-3, and MMP-10," Ann. Rheum. Dis., vol. 61, pp. 975-980 (2002).

(56) References Cited

OTHER PUBLICATIONS

Travers et al., "Extensive citrullination Promotes Immunogenicity of HSP90 through Protein Unfolding and Exposure of Cryptic Epitopes," J. of Immunol., vol. 197, pp. 926-1936 (2016).

Ubl et al., "14-3-3 protein is a component of Lewy bodies in Parkinson's disease—Mutation analysis and association studies of 14-3-3 eta," Molecular Brain Research, vol. 108, pp. 33-39 (2002).

Umahara et al., "Intranuclear localization and isoform-dependent translocation of 14-3-3 proteins in human brain with infarction," J. Neurology Sciences, vol. 260, pp. 159-166 (2007).

Van Everbroeck et al., "14-3-3 γ-isoform detection distinguishes sporadic Creutzfeldt-Jakob disease from other dementias," J. Neurology Neurosurgery and Psychiatry vol. 76, pp. 100-102 (2005).

Van Herwijnen et al., "Heat shock proteins can be targets of regulatory T cells for therapeutic intervention in rheumatoid arthritis," International Journal of Hyperthermia, vol. 29(5), pp. 448-454 (2013).

Vierboom et al., "Preclinical models of arthritic disease in non-human primates," Drug Discovery Today, vol. 12, pp. 327-335 (2007).

Wadhwa et al., "Neutralizing antibodies to granulocyte-macrophage colony-stimulating factor, interleukin-1α and interferon-α but not other cytokines in human immunoglobulin preparations," Immunology, vol. 99, pp. 113-123 (2000).

Wang et al., "Isolation of high-affinity peptide antagonists of 14-3-3 proteins by phage display," Biochemistry, vol. 38, pp. 12499-12504 (1999).

Wilker et al., "14-3-3 Proteins—a focus on cancer and human disease," J. Mo. Cell Cardiol., vol. 37(3), pp. 633-642 (2004).

Williams, Richard O., "Collagen-induced arthritis as a model for rheumatoid arthritis," Methods Mol. Med. vol. 98, pp. 207-216 (2004).

Wakabayashi et al., "Increased concentrations of 14-3-3ε, γ and ζ isoforms in cerebrospinal fluid of AIDS patients with neuronal destruction," Clinica Chimica Acta, 312: pp. 97-105 (2001).

Xiao et al., "An approach to studying lung cancer-related proteins in human blood," Molecular & Cellular Proteomics, vol. 4, pp. 1480-1486 (2005).

Yaffe, Micahel B., "How do 14-3-3 proteins work?—Gatekeeper phosphorylation and the molecular anvil hypothesis," FEBS Lett., vol. 513(1), pp. 53-57 (2002).

Yamamura et al., "Effector function of resting T cells: activation of synovial fibroblasts," J. Immunol., vol. 166, pp. 2270-2275 (2001).

Yao et al., "Intra-articular injection of recombinant TRAIL induces synovial apoptosis and reduces inflammation in a rabbit knee model of arthritis," Arthritis Research and Therapy, vol. 8(1), pp. 1-8 (2006).

\* cited by examiner

SEQUENCE LISTING

```
<160> NUMBER OF SEQ ID NOS: 27

<210> SEQ ID NO 1
<211> LENGTH: 246
<212> TYPE: PRT
<213> ORGANISM: Homo sapiens

<400> SEQUENCE: 1

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220
```

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 2
<211> LENGTH: 245
<212> TYPE: PRT
<213> ORGANISM: Homo sapiens

<400> SEQUENCE: 2

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 3
<211> LENGTH: 255
<212> TYPE: PRT
<213> ORGANISM: Homo sapiens

<400> SEQUENCE: 3

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

```
Tyr Lys Asn Val Ile Gly Ala Arg Arg Ala Ser Trp Arg Ile Ile Ser
 50                  55                  60

Ser Ile Glu Gln Lys Glu Glu Asn Lys Gly Glu Asp Lys Leu Lys
 65                  70                  75                  80

Met Ile Arg Glu Tyr Arg Gln Met Val Glu Thr Glu Leu Lys Leu Ile
                 85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Lys Met Lys Gly Asp Tyr
                115                 120                 125

His Arg Tyr Leu Ala Glu Phe Ala Thr Gly Asn Asp Arg Lys Glu Ala
130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 4
<211> LENGTH: 247
<212> TYPE: PRT
<213> ORGANISM: Homo sapiens

<400> SEQUENCE: 4

Met Val Asp Arg Glu Gln Leu Val Gln Lys Ala Arg Leu Ala Glu Gln
 1               5                  10                  15

Ala Glu Arg Tyr Asp Asp Met Ala Ala Ala Met Lys Asn Val Thr Glu
                 20                  25                  30

Leu Asn Glu Pro Leu Ser Asn Glu Glu Arg Asn Leu Leu Ser Val Ala
                 35                  40                  45

Tyr Lys Asn Val Val Gly Ala Arg Arg Ser Ser Trp Arg Val Ile Ser
 50                  55                  60

Ser Ile Glu Gln Lys Thr Ser Ala Asp Gly Asn Glu Lys Lys Ile Glu
 65                  70                  75                  80

Met Val Arg Ala Tyr Arg Glu Lys Ile Glu Lys Glu Leu Glu Ala Val
                 85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
                115                 120                 125

Asp Tyr Tyr Arg Tyr Leu Ala Glu Val Ala Thr Gly Glu Lys Arg Ala
                130                 135                 140

Thr Val Val Glu Ser Ser Glu Lys Ala Tyr Ser Glu Ala His Glu Ile
145                 150                 155                 160
```

```
Ser Lys Glu His Met Gln Pro Thr His Pro Ile Arg Leu Gly Leu Ala
            165                 170                 175

Leu Asn Tyr Ser Val Phe Tyr Tyr Glu Ile Gln Asn Ala Pro Glu Gln
            180                 185                 190

Ala Cys His Leu Ala Lys Thr Ala Phe Asp Asp Ala Ile Ala Glu Leu
            195                 200                 205

Asp Thr Leu Asn Glu Asp Ser Tyr Lys Asp Ser Thr Leu Ile Met Gln
            210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
            245

<210> SEQ ID NO 5
<211> LENGTH: 246
<212> TYPE: PRT
<213> ORGANISM: Homo sapiens

<400> SEQUENCE: 5

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
            85                  90                  95

Cys Asn Asp Val Leu Ser Leu Leu Asp Lys Phe Leu Ile Lys Asn Cys
            100                 105                 110

Asn Asp Phe Gln Tyr Glu Ser Lys Val Phe Tyr Leu Lys Met Lys Gly
            115                 120                 125

Asp Tyr Tyr Arg Tyr Leu Ala Glu Val Ala Ser Gly Glu Lys Lys Asn
            130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
            165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
            195                 200                 205

Asp Thr Leu Asn Glu Asp Ser Tyr Lys Asp Ser Thr Leu Ile Met Gln
            210                 215                 220

Leu Leu Arg Asp Asn Leu Thr Leu Trp Thr Ser Asp Gln Gln Asp Glu
225                 230                 235                 240

Glu Ala Gly Glu Gly Asn
            245

<210> SEQ ID NO 6
<211> LENGTH: 245
<212> TYPE: PRT
<213> ORGANISM: Homo sapiens
```

-continued

```
<400> SEQUENCE: 6

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Arg Asn Leu Leu Ser Val Ala Tyr
        35                  40                  45

Lys Asn Val Val Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
    210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 7
<211> LENGTH: 248
<212> TYPE: PRT
<213> ORGANISM: Homo sapiens

<400> SEQUENCE: 7

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110
```

```
Asp Ala Glu Ser Arg Val Phe Tyr Leu Lys Met Lys Gly Asp Tyr Tyr
            115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 8
<211> LENGTH: 12
<212> TYPE: PRT
<213> ORGANISM: Homo sapiens

<400> SEQUENCE: 8

Met Gly Asp Arg Glu Gln Leu Leu Gln Arg Ala Arg
1               5                   10

<210> SEQ ID NO 9
<211> LENGTH: 12
<212> TYPE: PRT
<213> ORGANISM: Homo sapiens

<400> SEQUENCE: 9

Met Gly Asp Arg Glu Gln Leu Leu Gln Arg Ala Arg
1               5                   10

<210> SEQ ID NO 10
<211> LENGTH: 15
<212> TYPE: PRT
<213> ORGANISM: Homo sapiens

<400> SEQUENCE: 10

Arg Glu Gln Leu Leu Gln Arg Ala Arg Leu Ala Glu Gln Ala Glu
1               5                   10                  15

<210> SEQ ID NO 11
<211> LENGTH: 15
<212> TYPE: PRT
<213> ORGANISM: Homo sapiens

<400> SEQUENCE: 11

Arg Leu Ala Glu Gln Ala Glu Arg Tyr Asp Asp Met Ala Ser Ala
1               5                   10                  15

<210> SEQ ID NO 12
<211> LENGTH: 18
<212> TYPE: PRT
<213> ORGANISM: Homo sapiens
```

-continued

```
<400> SEQUENCE: 12

Lys Ala Val Thr Glu Leu Asn Glu Pro Leu Ser Asn Glu Asp Arg Asn
1               5                   10                  15

Leu Leu

<210> SEQ ID NO 13
<211> LENGTH: 20
<212> TYPE: PRT
<213> ORGANISM: Homo sapiens

<400> SEQUENCE: 13

Lys Asn Val Val Gly Ala Arg Arg Ser Ser Trp Arg Val Ile Ser Ser
1               5                   10                  15

Ile Glu Gln Lys
            20

<210> SEQ ID NO 14
<211> LENGTH: 13
<212> TYPE: PRT
<213> ORGANISM: Homo sapiens

<400> SEQUENCE: 14

Lys Lys Leu Glu Lys Val Lys Ala Tyr Arg Glu Lys Ile
1               5                   10

<210> SEQ ID NO 15
<211> LENGTH: 19
<212> TYPE: PRT
<213> ORGANISM: Homo sapiens

<400> SEQUENCE: 15

Lys Asp Ser Thr Leu Ile Met Gln Leu Leu Arg Asp Asn Leu Thr Leu
1               5                   10                  15

Trp Thr Ser

<210> SEQ ID NO 16
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Citrulline

<400> SEQUENCE: 16

Met Gly Asp Xaa Glu Gln Leu Leu Gln Arg Ala Arg
1               5                   10

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Citrulline

<400> SEQUENCE: 17

Arg Glu Gln Leu Leu Gln Arg Ala Xaa Leu Ala Glu Gln Ala Glu
1               5                   10                  15
```

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Citrulline

<400> SEQUENCE: 18

Arg Leu Ala Glu Gln Ala Glu Xaa Tyr Asp Asp Met Ala Ser Ala
1               5                   10                  15

<210> SEQ ID NO 19
<211> LENGTH: 18
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Citrulline

<400> SEQUENCE: 19

Lys Ala Val Thr Glu Leu Asn Glu Pro Leu Ser Asn Glu Asp Xaa Asn
1               5                   10                  15

Leu Leu

<210> SEQ ID NO 20
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Citrulline

<400> SEQUENCE: 20

Lys Asn Val Val Gly Ala Arg Arg Ser Ser Trp Xaa Val Ile Ser Ser
1               5                   10                  15

Ile Glu Gln Lys
            20

<210> SEQ ID NO 21
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Citrulline

<400> SEQUENCE: 21

Lys Lys Leu Glu Lys Val Lys Ala Tyr Xaa Glu Lys Ile
1               5                   10

<210> SEQ ID NO 22
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Citrulline

```
<400> SEQUENCE: 22

Lys Asp Ser Thr Leu Ile Met Gln Leu Leu Xaa Asp Asn Leu Thr Leu
1               5                   10                  15

Trp Thr Ser

<210> SEQ ID NO 23
<211> LENGTH: 9
<212> TYPE: PRT
<213> ORGANISM: Homo sapiens

<400> SEQUENCE: 23

Met Gly Asp Arg Glu Gln Leu Leu Gln
1               5

<210> SEQ ID NO 24
<211> LENGTH: 9
<212> TYPE: PRT
<213> ORGANISM: Homo sapiens

<400> SEQUENCE: 24

Gln Ala Glu Arg Tyr Asp Asp Met Ala
1               5

<210> SEQ ID NO 25
<211> LENGTH: 10
<212> TYPE: PRT
<213> ORGANISM: Homo sapiens

<400> SEQUENCE: 25

Asp Arg Asn Leu Leu Ser Val Ala Tyr Lys
1               5                   10

<210> SEQ ID NO 26
<211> LENGTH: 10
<212> TYPE: PRT
<213> ORGANISM: Homo sapiens

<400> SEQUENCE: 26

Ser Ser Trp Arg Val Ile Ser Ser Ile Glu
1               5                   10

<210> SEQ ID NO 27
<211> LENGTH: 13
<212> TYPE: PRT
<213> ORGANISM: Homo sapiens

<400> SEQUENCE: 27

Ala Val Thr Glu Leu Asn Glu Pro Leu Ser Asn Glu Asp
1               5                   10
```

ANTIGENS DERIVED FROM CITRULLINATED 14-3-3 AND USES THEREOF IN THE DIAGNOSIS OF RHEUMATOID ARTHRITIS

SEQUENCE LISTING

The instant application contains a Sequence Listing which has been submitted electronically in ASCII format and is hereby incorporated by reference in its entirety. Said ASCII copy, created on Feb. 2, 2017, is named 177073_PCT_US_SL.txt and is 19,782 bytes in size.

FIELD OF INVENTION

The present invention relates generally to citrullinated peptides specifically bound by serum autoantibody, and anti-14-3-3 autoantibodies in particular, present in the serum of patients suffering from arthritic conditions. Such peptides comprise a citrullinated 14-3-3 eta sequence, or portion thereof, in which an arginine in the native sequence has been determinated to a citrulline. The invention also concerns the use of these peptides to evaluate arthritic conditions including rheumatoid arthritis and antibodies directed to these citrullinated peptides.

BACKGROUND OF THE INVENTION

Arthritis, or arthralgia, generally refers to inflammatory disorders of the joints of the body, and is usually accompanied by pain, swelling and stiffness. Arthritis may result from any of several causes including infections, trauma, degenerative disorders, metabolic disorders or disturbances or other unknown etiologies.

Rheumatoid Arthritis (RA), for example, is a chronic inflammatory disorder of the synovial membranes, and is one of the most common systemic autoimmune diseases. The diagnosis of RA depends primarily on clinical manifestations, but laboratory results are helpful in differential diagnosis and disease management. Early diagnosis of RA is important both in disease treatment and management. Kim and Weisman (2000) *Arthritis. Rheum.* 43:473-84.

The serum of affected patients contains factors that may be markers for the disease, allowing for early diagnosis. Historically, rheumatoid factor (RF) has long been one of the primary serologic indicators for RA. Additionally, anti-keratin autoantibodies (AKA), also known as anti-perinuclear autoantibodies, are detected in 40-55% of RA patients and in 40-50% of clinically diagnosed RA patients who are RF negative. Vincent et al. (1989) *Ann. Rheum. Dis.* 48:712-22; Corconnier et al. (1996) *Br. J. Rheumatol.* 35:620-4; Gabay et al. (1993) *Ann. Rheum. Dis.* 52:785-9. AKA is generally considered to be significantly more specific than RF. Additionally, AKA may precede the clinical appearance of RA by months or years. PCT Publication No. 2010102412 entitled "Compositions and Methods for Characterizing Arthritic Conditions" also describes autoantibodies to 14-3-3 proteins and methods of using them to evaluate arthritic conditions such as RA. For example, 14-3-3 eta is normally an intracellular protein and only in the disease state is it released into the extracellular space. As such, serum 14-3-3 eta and/or autoantibodies to same have diagnostic utility as markers that complement other serologic indicators in early and established RA and are associated with joint damage in RA and PsA, Recently it was determined that AKA recognize an epitope that contains citrulline. von Venrooj (2000) *Arthritis Res.* 52:785-9. Citrullination is a form of a post-translational modification (PTM) whereby peptidylarginine deiminases (PAD) catalyze the deimination of the amino acid arginine (R) to citrulline (C) resulting in a chemical change liberating a nitrogen-based moiety. Disregulated citrullination appears to be an active process in inflammatory conditions like RA whereby an "insult" results in 1) activation of PAD; 2) release of PAD enzymes into the synovial space; 3) citrullination of extracellular proteins like vimentin and filaggrin; 4) a humoral immune response against the citrullinated antigens and 5) the perpetuation of the disease. Detection of these anti-citrullinated antibodies may also be useful in the early diagnosis of RA.

IgG antibodies against a synthetic peptide containing citrulline known as CCP (Cyclic Citrullinated Peptide) has proven to be better than either AKA or RF testing in differentiating RA from other autoimmune diseases, and the presence of anti-CCP antibody occurs independently of elevated RF levels in patients with RA. However, a significant percentage of patients are or remain seronegative for anti-CCP. Accordingly, there remains a significant need in the art for better and more specific diagnostic indicators of this disease.

SUMMARY OF INVENTION

As disclosed herein, the citrullination sites of human 14-3-3 eta were identified in silico, in vitro, and using clinical samples. The citrullinated form of 14-3-3 eta and/or anti-14-3-3 autoantibodies specific for these post-translational modifications compared to the native or non-citrullinated form of 14-3-3 eta may be used for the diagnosis and prognosis of rheumatoid arthritis, including in anti-CCP negative patients. In particular, and as disclosed herein for the first time, 14-3-3 eta represents a novel citrullination target that is differentially expressed in anti-CCP negative RA patients versus healthy controls, indicating that detection of the citrullinated protein, and/or autoantibodies specific for citrullinated-14-3-3 eta may significantly improve RA diagnosis.

Accordingly, the invention provides compositions comprising a citrullinated 14-3-3 eta protein or a citrullinated fragment thereof and methods of using same, e.g., for the diagnosis and prognosis of rheumatoid arthritis. Also provided herein are compositions comprising monoclonal antibodies that selectively bind to a citrullinated 14-3-3 eta protein and/or to a specific citrullination site within said protein, as opposed to the corresponding native or noncitrullinated form, and methods of using same.

In one aspect, the present invention concerns the finding that the presence/quantity of autoantibodies directed against the citrullinated form of 14-3-3 eta in a biological sample is indicative of the existence and/or status of the arthritic condition in the subject. Also provided herein are methods for evaluating and/or characterizing an arthritic condition in a mammalian subject comprising detecting circulating immune complexes with at least one citrullinated 14-3-3 eta protein or a fragment thereof in a biological sample from a subject.

In preferred embodiments, the citrullinated 14-3-3 eta protein or fragment thereof comprises at least one citrulline residue at least one citrullination site, preferably selected from the group consisting of position 4, position 12, position 19, position 42, position 61, position 86 or position 227 of the native 14-3-3 eta sequence, or combinations thereof. The citrullinated 14-3-3 eta protein or fragment thereof may be isolated or, more preferably, bound to a solid support as described in more detail herein.

Accordingly, described herein are methods for evaluating and/or characterizing an arthritic condition in a mammalian subject comprising contacting a biological sample from the subject with at least one citrullinated 14-3-3 eta protein or fragment thereof and detecting an autoantibody against the citrullinated 14-3-3 eta protein or fragment thereof, wherein the presence/quantity of an autoantibody against said at least one citrullinated 14-3-3 eta protein or fragment thereof is indicative of the existence and/or status of the arthritic condition in the subject. Also provided herein are methods for evaluating and/or characterizing an arthritic condition in a mammalian subject comprising detecting circulating immune complexes between an autoantibody and at least one citrullinated 14-3-3 eta protein in a biological sample from the subject, wherein the presence/quantity of existing immune complexes in the sample is indicative of the existence and/or status of the arthritic condition in the subject.

In one embodiment, the detecting step includes quantifying/measuring the level of autoantibodies against, or immune complexes with, citrullinated 14-3-3 eta protein or a fragment thereof in the biological sample for comparison with a control sample. Accordingly, the presently-claimed methods for evaluating an arthritic condition in a subject may provide prognostic as well as diagnostic determinations.

In one aspect, the control sample is a normal control, and the comparison is indicative of an arthritis diagnosis. In one embodiment, an increased level of autoantibody against, or immune complexes with, citrullinated 14-3-3 eta protein or a fragment thereof in said biological sample in comparison with a normal control sample (e.g., from another subject not having an arthritic condition) is a diagnostic indicator of an arthritic condition in said subject.

Accordingly, in some embodiments, the presence of autoantibodies to citrullinated 14-3-3 eta protein or immune complexes thereof in the biological sample from the subject and/or the presence of an increased level of such autoantibodies or immune complexes in the biological sample from the subject relative to a level of such autoantibodies or immune complexes in a normal (i.e. non-arthritic) control sample provides a diagnosis that the subject has an arthritic condition.

In one aspect, the control sample is a previous biological sample from the mammalian subject, and the comparison is indicative of disease progression and/or efficacy of a therapeutic regimen. In one embodiment, a decreased level of autoantibodies to citrullinated 14-3-3 eta or circulating immune complexes thereof in said sample compared to the previous sample (e.g., a baseline biological sample from said subject) is indicative of the efficacy of an ongoing therapeutic regimen. In another embodiment, an increased level of autoantibodies to citrullinated 14-3-3 eta or circulating immune complexes thereof in said sample compared to the previous sample is indicative of a lack of a response to a therapeutic regimen.

Accordingly, in some embodiments, the relative level of autoantibodies against, or immune complexes with, citrullinated 14-3-3 eta or a fragment thereof detected in the biological sample from the subject compared to the level of such autoantibodies or complexes present in a baseline biological sample from the same subject provides a prognostic indication of the arthritic condition, and/or a theranostic indication of the potential efficacy of a proposed therapeutic regimen.

In one aspect, the control sample is the same biological sample from the mammalian subject, and the comparison is with the relative level or amount of autoantibodies directed to native or non-citrullinated 14-3-3 eta, which can also be indicative of disease progression and/or the efficacy of a potential therapeutic regimen as described herein. In one embodiment, increased levels of autoantibodies to citrullinated 14-3-3 eta or circulating immune complexes thereof in said sample compared to the levels of autoantibodies to native or non-citrullinated 14-3-3 eta or circulating immune complexes thereof in the same sample is indicative of the staging and/or prognosis of the disease, or suggestive of potential therapeutic interventions (e.g. inhibitors that directly target peptidyl arginine deminiases and the like).

Accordingly, in some embodiments, the relative level of autoantibodies against, or immune complexes with, citrullinated 14-3-3 eta or a fragment thereof detected in the biological sample from the subject compared to the level of autoantibodies or complexes to the native or non-citrullinated form in the same or sequential biological sample(s) from the subject provides a prognostic indication of the arthritic condition, and/or a theranostic indication of the potential efficacy of a proposed therapeutic regimen.

In one aspect, the control sample is an arthritic control, and the comparison is indicative of disease prognosis. In one embodiment, the relative level of autoantibodies to citrullinated 14-3-3 eta or immune complexes thereof in comparison to an arthritic control sample (e.g., from another subject with a well-defined arthritic condition) is a prognostic indicator of arthritis.

Accordingly, in some embodiments, subjects with different arthritic status have detectable differences in levels of autoantibodies to at least one citrullinated 14-3-3 eta protein or fragment thereof, and/or circulating immune complexes of such, and these differences are of prognostic relevance. In one example, disclosed herein are methods that may be used to determine a specific disease stage or the histopathological phenotype of an arthritic condition based on the relative level of autoantibody detected in a subject compared to levels previously determined to exist throughout the course of the arthritic condition, e.g., before treatment, during treatment, after treatment, in another patient, etc. In another example, the methods disclosed herein may be used to classify a biological sample as being from a subject at high risk for manifestation of an arthritic condition based on the relative level of autoantibodies detected in the biological sample compared to a control sample, which may be, e.g., stored in a database.

In another aspect, the methods disclosed herein may be used for theranostic purposes, e.g., to predict the responsiveness of a subject to a proposed therapeutic regimen based on the relative level of autoantibodies detected in a biological sample from the subject compared to a control sample, e.g., of a second biological sample from a second subject that was successfully treated with the proposed therapeutic regimen.

Accordingly, in some embodiments, the relative level of autoantibodies against, or immune complexes with, at least one citrullinated 14-3-3 eta protein or fragment thereof in the biological sample from the first subject is compared to the level of autoantibodies against, or immune complexes with, citrullinated 14-3-3 eta in biological samples from subjects whose abilities to respond to a treatment are known, wherein such comparison determines the response potential of the first subject to the treatment. Determination of the sensitivity of the subject to a therapeutic regimen may then be used to inform methods of treating a subject with an arthritic condition. For example, described herein are methods of treating a subject with an arthritic condition comprising measuring the level of autoantibody against citrullinated 14-3-3 eta in a biological sample from the subject (e.g., by measuring the level of autoantibody/citrullinated 14-3-3 eta immune complex formation), correlating the level of autoantibody against or immune complex with citrullinated 14-3-3 eta with sensitivity of the subject to a therapeutic regimen, and providing the therapeutic regimen to the subject. In one aspect, the invention provides methods for monitoring treatment of an arthritic condition, comprising determining the level of autoantibodies against, or immune complexes with, at least one citrullinated 14-3-3 eta protein or fragment thereof in patient samples and monitoring the level of autoantibodies/immune complexes involving citrullinated 14-3-3 eta in a patient undergoing treatment.

In another aspect, provided herein are methods for determining and/or differentiating the subtypes of arthritis in a patient. In this aspect, the relative level of autoantibodies against, or immune complexes with, at least one citrullinated 14-3-3 eta protein or fragment thereof in the biological sample from the first subject is compared to the level of autoantibodies against, or immune complexes with, citrullinated 14-3-3 eta in biological samples from one or more other subjects whose subtype of arthritis is known and/or previously-established, wherein such comparison determines the subtype of arthritis for the first subject.

Determination that the levels of autoantibodies against, or immune complexes with, at least one citrullinated 14-3-3 protein or fragment thereof in the biological sample from the first subject are similar to the levels of autoantibodies against, or immune complexes with, at least one citrullinated 14-3-3 protein or fragment thereof in the biological sample from in the biological sample of another subject whose subtype of arthritis is known and/or previously-established may indicate that the first subject has the same subtype of arthritis as the other subject. For example, similar levels of autoantibodies against, or immune complexes with, at least one citrullinated 14-3-3 protein or fragment thereof in the biological sample from the first subject and in the biological sample of another subject known to have inflammatory arthritis, e.g., Rheumatoid arthritis, may determine that the first subject also has inflammatory arthritis, e.g., Rheumatoid arthritis.

Additionally, determination that the levels of autoantibodies against, or immune complexes with, at least one citrullinated 14-3-3 protein or fragment thereof in the biological sample from the first subject are dissimilar to the levels of autoantibodies against, or immune complexes with, at least one citrullinated 14-3-3 protein or fragment thereof in the biological sample from another subject whose subtype of arthritis is known and/or previously-established may indicate that the first subject has a subtype of arthritis different than that of the other subject. For example, dissimilar levels of autoantibodies against, or immune complexes with, at least one citrullinated 14-3-3 protein or fragment thereof in the biological sample from the first subject and in the biological sample of another subject known to have noninflammatory arthritis, e.g., osteoarthritis, may determine that the first subject has an inflammatory arthritis, e.g., Rheumatoid arthritis.

In one embodiment, the detecting step comprises an immunological-based technique, e.g., immunoprecipitation, ELISA, Western blot analysis, immunohistochemistry, immunofluorescence, "sandwich" immunoassays, immunoradiometric assays, gel diffusion precipitation reactions, immunodiffusion assays, in situ immunoassays, precipitation reactions, agglutination assays, complement fixation assays, protein A assays, Immunoelectrophoresis assays, fluorescence activated cell sorting (FACS) analysis, radioimmunoassay, and the like.

Detecting and/or measuring autoantibodies against a citrullinated 14-3-3 protein or fragment thereof according to the methods described herein may thus be performed by observing the formation of an immune complex between the autoantibody and citrullinated 14-3-3 or fragment thereof in a sample, or alternatively determining the presence of an existing autoantibody/citrullinated 14-3-3 complex in a sample. In one embodiment, the formation may be detected by way of detectably labeled citrullinated 14-3-3 protein(s) or fragment(s) thereof. In another embodiment, the complex may be detected by forming a second immune complex between the autoantibody/citrullinated 14-3-3 complex and a detectably labeled secondary antibody that binds immunoglobulin, e.g., the immunoglobulin backbone of the autoantibody.

In one embodiment, the methods involve detecting autoantibodies against citrullinated 14-3-3 or circulating immune complexes thereof in the blood, synovial fluid, plasma, serum, or tissue (e.g. synovial joint, damaged joint tissue, etc.) of a patient. In one embodiment, detection is done by immunoprecipitation of autoantibodies against citrullinated 14-3-3 from blood, synovial fluid, plasma, serum or tissue using citrullinated 14-3-3 protein or fragment thereof. In one embodiment, detection involves the use of ELISA. In one embodiment, detection involves Western blot analysis of a sample comprising synovial fluid, plasma, or serum from a patient. In one embodiment, detection involves the use of radioimmunoassay. In one embodiment, detection involves the use of a strip test. In one embodiment, detection involves the use of a point of care test. In one embodiment, detection of autoantibodies against citrullinated 14-3-3 or circulating complexes thereof is combined with detection of another marker of arthritis (e.g., MMP, anti-CCP, anti-RF and/or CRP).

Also described herein are kits comprising a reagent for evaluating an arthritic condition in a subject, wherein the reagent specifically recognizes autoantibodies to citrullinated 14-3-3 protein or a fragment thereof. In one embodiment, the reagent may include a detectably labeled citrullinated 14-3-3 protein or fragment thereof, which may also be immobilized on a solid support. The citrullinated 14-3-3 protein or fragment thereof may comprise an epitope shared between a plurality of 14-3-3 protein isoforms, or may comprise an epitope unique to one or a subset of citrullinated 14-3-3 protein isoforms. In preferred embodiments, the citrullinated 14-3-3 protein or fragment thereof comprises a citrullinated 14-3-3 eta and/or gamma epitope. In one embodiment, the citrullinated 14-3-3 protein or fragment thereof comprises a citrullinated 14-3-3 eta epitope shared by at least one other citrullinated 14-3-3 isoform, e.g. 14-3-3 gamma. In another embodiment, the citrullinated 14-3-3 eta epitope is unique to 14-3-3 eta.

In another aspect, provided herein is an antibody capable of binding selectively to a citrullinated human 14-3-3 protein or a citrullinated fragment thereof, over the native human 14-3-3 eta protein or native human 14-3-3 eta fragment thereof, respectively. In a preferred embodiment, the isolated antibody competes for binding to a citrullinated 14-3-3 eta protein with anti-14-3-3 eta autoantibodies specific for the citrullinated 14-3-3 eta protein but not with anti-14-3-3 eta autoantibodies specific for the native or non-citrullinated form of the 14-3-3 eta protein.

In one embodiment, the antibody is capable of binding selectively to citrullinated 14-3-3 eta protein or a citrullinated fragment thereof, over native 14-3-3 eta protein or native 14-3-3 eta fragment thereof, respectively In a preferred embodiment, the antibody is capable of selectively binding a citrullinated 14-3-3 eta protein comprising an amino acid sequence selected from the group consisting of SEQ ID NOs:16-22 over a native 14-3-3 eta protein comprising an amino acid sequence selected from the group consisting of SEQ ID NOs:9-15, respectively. In one embodiment, an antibody provided herein selectively binds a protein comprising the amino acid sequence of SEQ ID NO:16, but not a protein comprising the amino acid sequence of SEQ ID NO:9. In one embodiment, an antibody provided herein selectively binds a protein comprising the amino acid sequence of SEQ ID NO:17, but not a protein comprising the amino acid sequence of SEQ ID NO:10. In one embodiment, an antibody provided herein selectively binds a protein comprising the amino acid sequence of SEQ ID NO:18, but not a protein comprising the amino acid sequence of SEQ ID NO:11. In one embodiment, an antibody provided herein selectively binds a protein comprising the amino acid sequence of SEQ ID NO:19, but not a protein comprising the amino acid sequence of SEQ ID NO:12. In one embodiment, an antibody provided herein selectively binds a protein comprising the amino acid sequence of SEQ ID NO:20, but not a protein comprising the amino acid sequence of SEQ ID NO:13. In one embodiment, an antibody provided herein selectively binds a protein comprising the amino acid sequence of SEQ ID NO:21, but not a protein comprising the amino acid sequence of SEQ ID NO:14. In one embodiment, an antibody provided herein selectively binds a protein comprising the amino acid sequence of SEQ ID NO:22, but not a protein comprising the amino acid sequence of SEQ ID NO:15. In another embodiment, the antibody is capable of selectively binding citrullinated 14-3-3 gamma protein over native 14-3-3 gamma protein.

In another aspect, the present invention concerns the finding that the degree of citrullination of individual 14-3-3 eta proteins, and/or the identification of citrulline resides at particular sites within the protein, e.g. at any one or more of positions 4, 12, 19, 42, 61, 86 and 227 of SEQ ID NO: 5, is also indicative of the existence and/or status of the arthritic condition in the subject. Also provided herein are methods for evaluating and/or characterizing an arthritic condition in a mammalian subject comprising detecting the degree and/or specific citrullination positions of at least one citrullinated 14-3-3 eta protein or a fragment thereof in a biological sample from a subject employing the aforementioned selective antibodies.

Accordingly, described herein are methods for evaluating and/or characterizing an arthritic condition in a mammalian subject comprising contacting a biological sample from the subject with one or more antibodies capable of binding selectively to a citrullinated human 14-3-3 eta protein or a citrullinated fragment thereof and detecting the citrullinated 14-3-3 eta protein or fragment thereof, wherein the presence, degree and/or location of citrullination within said 14-3-3 eta protein or fragment thereof is indicative of the existence and/or status of the arthritic condition in the subject, in comparison with a defined clinical test result standard.

DETAILED DESCRIPTION

Figure 1:
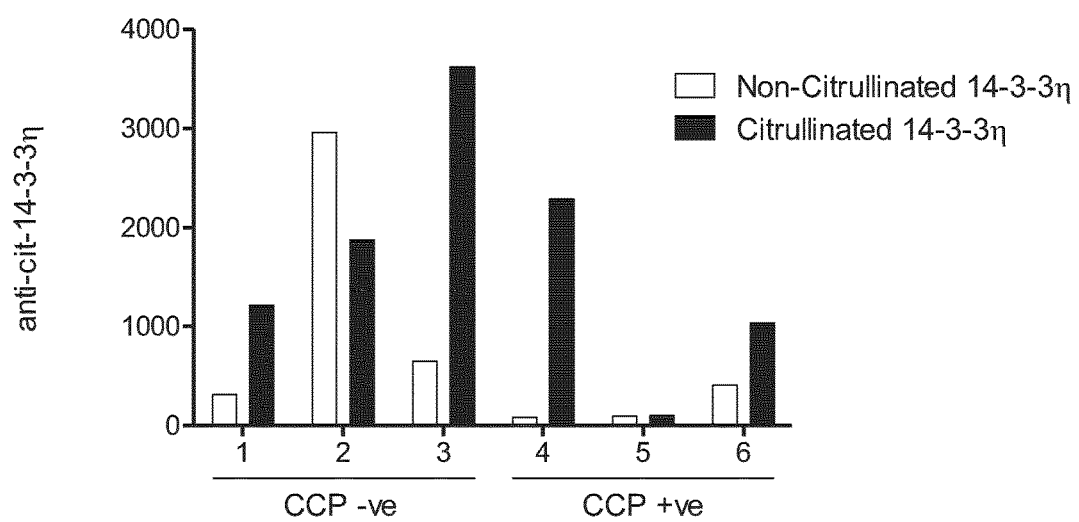
FIG. 1. shows a bar graph representing the 14-3-3 eta citrullination specific autoantibody response in anti-CCP negative ("CCP −ve") and anti-CCP positive ("CCP +ve") rheumatoid arthritis (RA) patients as measured by the autoantibody reactivity directed towards either the recombinant non-citrullinated or citrullinated form of the 14-3-3 eta antigen. 14-3-3 eta autoantibodies preferentially bind to the citrullinated form of the 14-3-3 eta antigen in both anti-CCP negative and positive patients.

"14-3-3" and "14-3-3 protein" are used interchangeably and refer to at least one member of the 14-3-3 family. A 14-3-3 protein is a member of a family of conserved intracellular regulatory molecules that are ubiquitously expressed in eukaryotes. 14-3-3 proteins have the ability to bind a multitude of functionally diverse signaling proteins, including kinases, phosphatases, and transmembrane receptors. Indeed, more than 100 signaling proteins have been reported as 14-3-3 ligands. 14-3-3 proteins may be considered evolved members of the Tetratrico Peptide Repeat superfamily. They generally have 9 or 10 alpha helices, and usually form homo- and/or hetero-dimer interactions along their amino-termini helices. These proteins contain a number of known domains, including regions for divalent cation interaction, phosphorylation and acetylation, and proteolytic cleavage, among others.

There are seven distinct genetically encoded isoforms of the 14-3-3 proteins that are known to be expressed in mammals, with each isoform comprising between 242-255 amino acids. The seven 14-3-3 protein isoforms are designated as 14-3-3 α/β (alpha/beta), 14-3-3 δ/ξ (delta/zeta), 14-3-3 ε (epsilon), 14-3-3 γ (gamma), 14-3-3 η (eta), 14-3-3 τ/θ (tau/theta), and 14-3-3 σ (sigma/stratifin). 14-3-3 proteins have a high degree of sequence similarity, and are known to undergo post-translational processing, e.g., phosphorylation, citrullination, etc. See, e.g., Megidish et al. (1998) *J. Biol. Chem.* 273: 21834-45. Consequently, anti-14-3-3 autoantibodies may specifically bind to and/or recognize more than one 14-3-3 protein isoform, or may specifically bind and/or recognize only one isoform (e.g., 14-3-3 eta).

Citrullination is a form of a post-translational modification (PTM) whereby peptidylarginine deiminases (PAD) catalyze the deimination of the amino acid arginine (R) to citrulline (C) resulting in a chemical change liberating a nitrogen-based moiety. Accordingly, the terms "citrullinated 14-3-3 protein" and "citrullinated 14-3-3 peptide" are interchangeable and refer to a protein that has an amino acid sequence that is identical to the amino acid sequence of a native 14-3-3 protein (e.g., a 14-3-3 protein that has not been modified post-translationally) but for the substitution of at least one arginine residue in the native sequence with a citrulline residue in the citrullinated sequence.

"Substituted by" or "replaced by" include modified into, e.g., an arginine residue that is substituted or replaced by a citrulline residue can also mean an arginine residue modified into a citrulline residue, e.g. by incubation with PAD. Citrullination by PAD starts mostly at the $NH_2$-terminus of the protein, but exceptionally it can start from the COOH terminus of the protein. In case several arginine residues are replaced by citrulline residues, this means that for said several arginine residues each single arginine residue is replaced by one single citrulline residue.

Peptidylarginine deiminases (PADs), also referred to as protein-arginine deiminases, are a family of posttranslational modification enzymes that convert arginine residues in peptides to citrulline residues in the presence of calcium ion.

"Citrulline" and "Cit" refers to 2-amino-5-(carbamoylamino)pentanoic acid and is an alfa-amino acid with formula: $H_2NC(O)NH(CH_2)_3CH(NH_2)CO_2H$.

The terms "peptide" and "protein" are interchangeable as used herein and refer to a molecule comprising an amino acid sequence of between 2 and 200 amino acids, connected by peptide bonds. Peptides may contain any of the conventional 20 amino acids or modified versions thereof and any non-naturally occurring amino-acids incorporated by chemical peptide synthesis or by chemical or enzymatic modification. Peptides may be used as antigens and may comprise one or more epitopes.

The term "derivative" "variant" and "fragment" as used herein with reference to a protein refers to molecules which comprises at least the active portion of said protein, e.g., comprises at least the epitope and/or the citrulline residue of said protein, either or both of which are specifically bound by anti-14-3-3 autoantibodies.

The term "epitope" refers to one or several portions (which may define a conformational epitope) of an antigenic protein which is/are specifically recognized and bound by an antibody or a portion thereof (Fab', Fab2', etc.) or a receptor presented at the cell surface of a B or T cell lymphocyte, and which is able, by said binding, to induce an immune response. Epitopes are chemical features generally present on surfaces of molecules and accessible to interaction with an antibody. Typical chemical features are amino acids and sugar moieties, having three-dimensional structural characteristics as well as chemical properties including charge, hydrophilicity, and lipophilicity. Conformational epitopes are distinguished from non-conformational epitopes by loss of reactivity with an antibody following a change in the spatial elements of the molecule without any change in the underlying chemical structure.

An ordinarily skilled artisan will recognize that autoantibodies recognize fragments of the antigen. Accordingly, as used herein, "fragment thereof" and "epitope" are used interchangeably and generally refer to a determinant of 14-3-3 that is capable of binding to an antibody, e.g., an autoantibody. Accordingly, the term "epitope" when used in reference to 14-3-3 proteins or specific isomers generally refers to a fragment of the protein, including a citrullinated 14-3-3 protein, that is capable of binding to an antibody, e.g., an autoantibody.

Described herein are citrullinated 14-3-3 epitopes that comprise at least one citrulline residue and are recognized by autoantibodies in a patient diagnosed with arthritis, particularly rheumatoid arthritis, methods of using such epitopes to evaluate and/or characterize an arthritic condition in a subject, and kits comprising such epitopes. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping.

"Antibody" refers to a composition comprising a protein that binds specifically to a corresponding antigen and has a common, general structure of immunoglobulins. The term antibody specifically covers polyclonal antibodies, monoclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. Typically, an antibody will comprise at least two heavy chains and two light chains interconnected by disulfide bonds, which when combined form a binding domain that interacts with an antigen. Each heavy chain is comprised of a heavy chain variable region (VH) and a heavy chain constant region (CH). The heavy chain constant region is comprised of three domains, CH1, CH2 and CH3, and may be of the mu, delta, gamma, alpha or epsilon isotype. Similarly, the light chain is comprised of a light chain variable region (VL) and a light chain constant region (CL). The light chain constant region is comprised of one domain, CL, which may be of the kappa or lambda isotype. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (CIq) of the classical complement system. The heavy chain constant region mediates binding of the immunoglobulin to host tissue or host factors, particularly through cellular receptors such as the Fc receptors (e.g., FcyRI, FcyRII, FcyRIII, etc.). As used herein, antibody also includes an antigen binding portion of an immunoglobulin that retains the ability to bind antigen. These include, as examples, F(ab), a monovalent fragment of VL CL and VH CH antibody domains; and $F(ab')_2$ fragment, a bivalent fragment comprising two Fab fragments linked by a disulfide bridge at the hinge region. The term antibody also refers to recombinant single chain Fv fragments (scFv) and bispecific molecules such as, e.g., diabodies, triabodies, and tetrabodies (see, e.g., U.S. Pat. No. 5,844,094).

"Antigen" is to be construed broadly and refers to any molecule, composition, or particle that can bind specifically to an antibody. An antigen may have one or more epitopes that interact with the antibody, although it does not necessarily induce production of that antibody.

"Autoantibodies" are endogenous antibodies that specifically bind self antigens, i.e., a normal tissue component. An autoantibody is produced in response to a naturally occurring antigen of the same body that produces the autoantibody. Accordingly, the terms "autoantibodies against 14-3-3" and "autoantibodies to 14-3-3" are used interchangeably and refer to endogenous antibodies produced by a mammalian subject that specifically bind a 14-3-3 protein, which may be citrullinated, or a fragment thereof from said host.

"Immunological binding" and "formation of an immune complex" are used interchangeably and as used in this context, generally refer to the non-covalent interactions of the type which occur between an antibody, e.g., an autoantibody, and an antigen for which the antibody is specific. The strength, or affinity of immunological binding interactions can be expressed in terms of the dissociation constant ($K_d$) of the interaction, wherein a smaller $K_d$ represents a greater affinity. Immunological binding properties can be quantified using methods well known in the art. For example, see Davies et al. (1990) Annual Rev. Biochem. 59:439-473. An antibody, or antigen-binding fragment thereof, is said to "specifically bind," "immunologically bind," and/or is "immunologically reactive" if it reacts at a detectable level (within, for example, an ELISA assay) with ligand, and does not react detectably with unrelated ligands under similar conditions.

The phrase "specifically (or selectively) binds" to an antibody, when referring to a protein or peptide, refers to a binding reaction that is determinative of the presence of the protein in a heterogeneous population of proteins and other biologics. The term "directed against" a protein or peptide, when referring to an antibody, refers also to the specific binding reaction that is determinative of the presence of the protein by said antibody in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Diagnostic" means identifying the presence or nature of a pathologic condition in a subject based on the presence or absence of one or more autoantibodies to the citrullinated 14-3-3 protein(s) disclosed herein. The diagnostic method makes the correlation between the presence of autoantibodies directed against citrullinated 14-3-3 protein(s) and the occurrence of a specific disease, e.g., rheumatoid arthritis, or a group of diseases (e.g. arthritic conditions).

"Prognostic" means determining the potential progression or outcome of a pathologic condition and/or disease process in a subject, with or without treatment, based on the presence/absence and/or amount of one or more autoantibodies to the citrullinated 14-3-3 protein(s) disclosed herein. The prognostic method makes the correlation between the presence and/or amount of autoantibodies directed against citrullinated 14-3-3 protein(s) and the progression and/or likely outcome of the arthritic condition.

"Theranostic" means determining the potential and/or likely reaction to a proposed treatment protocol for a pathologic condition and/or disease process in a subject, based on the presence/absence and/or amount of one or more autoantibodies to the citrullinated 14-3-3 protein(s) disclosed herein, and tailoring an appropriate treatment for the subject based on the results. The theranostic method makes the correlation between the presence and/or amount of autoantibodies directed against citrullinated 14-3-3 protein(s) and the likely efficacy of different treatment options on the arthritic condition in the subject.

"Subject" and "patient" are used interchangeably and refer to, except where indicated, mammals such as humans and non-human primates, as well as rabbits, rats, mice, goats, pigs, and other mammalian species.

"Arthritic condition," "arthritis," and "arthralgia" are used interchangeably, and generally refer to, except where indicated, an inflammatory disorder of the joints of the body. Pain, swelling, stiffness, and difficulty of movement are frequently associated with arthritic conditions. Arthritis consists of more than 100 different conditions. These can be anything from relatively mild forms to crippling systemic forms, see, e.g., www.arthritis.ca/types%20of%20arthritis/default.asp?s=1. An arthritic condition may result from any of several causes, including infection, trauma, degenerative disorders, metabolic disorders or disturbances, or other unknown etiologies.

An arthritic condition may be more specifically described according to the subtype, for example, rheumatoid arthritis, mixed connective tissue disease (MCTD), crystal induced arthritis, reactive arthritis, spondylarthropathy, osteoarthritis, sarcoidosis, palindromic rheumatism, post traumatic arthritis, malignancy related arthritis, septic arthritis, lyme arthritis, osteoarthritis, bacterial, infectious arthritis, etc. Arthritis may further accompany other identified disorders, including gout, ankylosing spondylitis, systemic lupus erythematosus, inflammatory bowel disease, psoriasis, etc. Well-defined arthritic condition refers to knowledge regarding the type of arthritis and its stage, e.g., onset, remission, relapse etc.

Citrullinated 14-3-3 Proteins

The amino acid sequences of native 14-3-3 proteins are set forth in Table 1. In some embodiments, a 14-3-3 protein is identical to the native 14-3-3 protein sequences provided in Table 1. The 14-3-3 protein may also be substantially homologous to a native 14-3-3 protein sequence provided in Table 1 and retain the functional activity of the 14-3-3 protein, e.g., specific binding to an anti-14-3-3 autoantibody, yet differs in amino acid sequence due to natural allelic variation or mutagenesis.

TABLE 1

14-3-3 proteins

| 14-3-3 Protein | NCBI Accession No. | SEQ ID NO: |
|---|---|---|
| 14-3-3 α/β | NP_003395.1 | 1 |
| 14-3-3 δ/ξ | NP_001129171.1 | 2 |
| 14-3-3 ε | NP_006752.1 | 3 |
| 14-3-3 γ | NP_036611.2 | 4 |
| 14-3-3 η | NP_003396.1 | 5 |
| 14-3-3 τ/θ | NP_006817.1 | 6 |
| 14-3-3 σ | NP_006133.1 | 7 |

As used herein, the phrase "14-3-3 eta protein" refers to a protein comprising SEQ ID NO: 5 as well as a protein substantially homologous thereto, e.g., a protein having at least 75%, yet more preferably 80% to 90%, still more preferably 90%-95%, again more preferable 95%, and most preferably at least 98% amino acid sequence identity with SEQ ID NO:5. The amino acid sequence of SEQ ID NO:5 is provided below.

```
MGDREQLLQR ARLAEQAERY DDMASAMKAV TELNEPLSNE
DRNLLSVAYK NVVGARRSSW RVISSIEQKT MADGNEKKLE
```

-continued

```
KVKAYREKIE KELETVCNDV LSLLDKFLIK NCNDFQYESK

VFYLKMKGDY YRYLAEVASG EKKNSVVEAS EAAYKEAFEI

SKEQMQPTHP IRLGLALNFS VFYYEIQNAP EQACLLAKQA

FDDAIAELDT LNEDSYKDST LIMQLLRDNL TLWTSDQQDE

EAGEGN
```

To determine the percent identity of two amino acid sequences or of two polynucleotide sequences, the sequences are aligned for optimal comparison purposes (e.g., gaps can be introduced in one or both of a first and a second amino acid or polynucleotide sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or polynucleotide "identity" is equivalent to amino acid or polynucleotide "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM 120 weight residue table, a gap length penalty of 12 and a gap penalty of 4.

The protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to polynucleotide molecules of the invention. BLAST protein searches can be performed with the XBLAST program, score=50, wordlength=3 to obtain amino acid sequences homologous to 14-3-3 protein molecules of the invention. To obtain gapped alignments for comparison purposes, Gapped BLAST can be utilized as described in Altschul et al., (1997) Polynucleotides Res. 25(17):3389-3402. When utilizing BLAST and Gapped BLAST programs, the default parameters of the respective programs (e.g., XBLAST and NBLAST) can be used, e.g., at www.ncbi.nim.nih.gov.

Incubation of a 14-3-3 protein, fragment, or fusion thereof with a peptidylarginine deiminase according to well-known methods results in a citrullinated 14-3-3 protein, fragment or fusion thereof. Such citrullinated 14-3-3 protein, fragment or fusion thereof can be used as an immunogen, to produce anti-14-3-3 antibodies, purify anti-14-3-3 antibodies, and in diagnostic, prognostic and theranostic assays as described herein.

In accordance with the present invention, the human 14-3-3 eta citrullination sites identified in silico, in vitro and using clinical samples are provided in Table 2.

TABLE 2

| AA Position | AA Sequence | Arginylated Peptide | Citrullinated Peptide |
|---|---|---|---|
| 4 | 1-12 | MGD[R]EQLLQRAR (SEQ ID NO: 9) | MGD[Cit]EQLLQRAR (SEQ ID NO: 16) |
| 12 | 4-18 | REQLLQRA[R]LAEQAE (SEQ ID NO: 10) | REQLLQRA[Cit]LAEQAE (SEQ ID NO: 17) |
| 19 | 12-26 | RLAEQAE[R]YDDMASA (SEQ ID NO: 1) | RLAEQAE[Cit]YDDMASA (SEQ ID NO: 18) |
| 42 | 29-45 | KAVTELNEPLSNED[R]NLL (SEQ ID NO: 12) | KAVTELNEPLSNED[Cit]NLL (SEQ ID NO: 19) |
| 61 | 50-69 | KNVVGARRSSW[R]VISSIEQK (SEQ ID NO: 13) | KNVVGARRSSW[Cit]VISSIEQK (SEQ ID NO: 20) |
| 86 | 77-89 | KKLEKVKAY[R]EKI (SEQ ID NO: 14) | KKLEKVKAY[Cit]EKI (SEQ ID NO: 21) |
| 227 | 217-235 | KDSTLIMQLL[R]DNLTLWTS (SEQ ID NO: 15) | KDSTLIMQLL[Cit]DNLTLWTS (SEQ ID NO: 22) |

Citrullinated proteins of the invention comprise at least citrulline residue at one of the amino acid positions listed in Table 2. In one embodiment, a citrullinated 14-3-3 eta fragment according to the present invention comprises an amino acid sequence selected from the group consisting of SEQ ID NOs: 16-22.

As shown in Table 3, several if not all of the seven citrullinated sites listed in Table 2 are conserved in other 14-3-3 isoforms as well. Accordingly, to the extent that these citrullination sites are conserved in other 14-3-3 isoforms, these sites may also be used to determine the citrullination status of these other 14-3-3 isoforms using the methods and materials disclosed herein.

TABLE 3

| Amino Acid Site in Eta | Eta | Gamma | Alpha/beta | Epsilon | Sigma | Theta | Zeta |
|---|---|---|---|---|---|---|---|
| 4 | Present | Present | No | Present | Present | No | No |
| 12 | Present | Present | No | No | No | No | No |
| 19 | Present | Present | Present | Present | Present | Present | Present |
| 42 | Present | Present | Present | Present | Present | Present | Present |
| 61 | Present | Present | Present | Present | Present | Present | Present |
| 86 | Present | Present | Present | Present | Present | Present | Present |
| 227 | Present | Present | Present | Present | Present | Present | Present |

Several aspects of the invention pertain to isolated citrullinated 14-3-3 proteins, and biologically active portions thereof, e.g., fragments suitable for use as antigens to anti-citrullinated 14-3-3 autoantibodies. Citrullinated 14-3-3 proteins, including fragments thereof, may be isolated from natural, recombinant or synthetic 14-3-3 protein (including fragments thereof, respectively), through the action of peptidylarginine deiminase, e.g., by incubating native 14-3-3 protein or fragments thereof, respectively, with peptidylarginine deiminases according to well-known methods. Alternatively, citrullinated 14-3-3 proteins may be isolated by peptide synthesis according to well-known methods, e.g., by directly incorporating citrulline residues into the peptide synthesized.

In one embodiment, 14-3-3 proteins can be isolated from cells or tissue sources by an appropriate purification scheme using standard protein purification techniques. In another embodiment, 14-3-3 proteins are produced by recombinant DNA techniques.

Preferably, a 14-3-3 protein or fragment thereof of the invention is produced by standard recombinant DNA techniques. For example, DNA fragments coding for the 14-3-3 protein or fragment thereof are ligated in an expression vector in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, PCR amplification of gene fragments can be carried out using anchor primers which give rise to complementary overhangs between two consecutive gene fragments which can subsequently be annealed and reamplified to generate a c gene sequence (see, e.g., Current Protocols In Molecular Biology, eds. Ausubel et al. John Wiley & Sons: 1992). Moreover, many expression vectors are commercially available that already encode a moiety, e.g., a detectable moiety. A polynucleotide encoding a 14-3-3 protein or fragment thereof can be cloned into such an expression vector such that a moiety, e.g., a detectable moiety, is linked in-frame to the 14-3-3 protein or fragment.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a polynucleotide sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods.

Alternatively, the signal sequence can be linked to the native or citrullinated 14-3-3 protein, fragment, or fusion thereof, using a sequence which facilitates purification, such as with a GST domain.

Antibodies to Citrullinated 14-3-3 Protein and Fragments Thereof

In other embodiments, the invention provides antibodies, i.e., intact antibodies and antigen binding fragments thereof, that specifically bind to a citrullinated 14-3-3 protein or fragment thereof, preferably mammalian (e.g., human) 14-3-3 protein, which may be useful in diagnosing, prognosing, monitoring and/or treating RA.

Antibody molecules to the polypeptides of the present invention, e.g., citrullinated 14-3-3 protein or citrullinated fragments thereof, may be produced by methods well known to those skilled in the art. For example, monoclonal antibodies may be produced by generation of hybridomas in accordance with known methods. Hybridomas formed in this manner are then screened using standard methods, such as an enzyme-linked immunosorbent assay (ELISA), to identify one or more hybridomas that produce an antibody that specifically binds with the polypeptides of the present invention. For example, a citrullinated 14-3-3 protein or a citrullinated fragment thereof of the invention may also be used to immunize non-human hosts, e.g., donkey, goat, sheep, guinea pig, hamster, rabbit, rat and mouse, to obtain polyclonal and monoclonal antibodies that react with the citrullinated 14-3-3 protein or a citrullinated fragment thereof but not the native 14-3-3 protein or native fragment thereof. The peptide immunogens additionally may contain a cysteine residue at the carboxyl terminus, and may be conjugated to a hapten such as keyhole limpet hemocyanin (KLH). Additional peptide immunogens may be generated by replacing tyrosine residues with sulfated tyrosine residues. Methods for synthesizing such peptides are well known in the art. A full-length polypeptide of the present invention may be used as the immunogen, or, alternatively, antigenic peptide fragments of the polypeptides may be used. An antigenic peptide of a polypeptide of the present invention comprises at least 7 continuous amino acid residues and encompasses an epitope such that an antibody raised against the peptide forms a specific immune complex with the polypeptide. Preferably, the antigenic peptide comprises at least 10 amino acid residues, more preferably at least 15 amino acid residues, even more preferably at least 20 amino acid residues, and most preferably at least 30 amino acid residues.

Monoclonal antibodies may be generated by other methods known to those skilled in the art of recombinant DNA technology. As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide related to the present invention (e.g., citrullinated 14-3-3 protein or a citrullinated fragment thereof) to thereby isolate immunoglobulin library members that bind to the polypeptides related to the present invention (e.g., citrullinated 14-3-3 protein or a citrullinated fragment thereof). Techniques and commercially available kits for generating and screening phage display libraries are well known to those skilled in the art. Additionally, examples of methods and reagents particularly amenable for use in generating and screening antibody display libraries can be found in the literature. For example, the "combinatorial antibody display" method is well known and was developed to identify and isolate antibody fragments having a particular antigen specificity, and can be utilized to produce monoclonal antibodies. After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers to a conserved 3' constant region, can be used for PCR amplification of the heavy and light chain variable regions from a number of murine antibodies; a similar strategy has also been used to amplify human heavy and light chain variable regions from human antibodies.

Polyclonal sera and antibodies may be produced by immunizing a suitable subject with a polypeptide of the present invention. The antibody titer in the immunized subject may be monitored over time by standard techniques, such as with ELISA using immobilized protein. If desired, the antibody molecules directed against a polypeptide of the present invention may be isolated from the subject or culture media and further purified by well-known techniques, such as protein A chromatography, to obtain an IgG fraction.

Fragments of antibodies to the polypeptides of the present invention may be produced by cleavage of the antibodies in accordance with methods well known in the art. For example, immunologically active Fab and F(ab').sub.2 fragments may be generated by treating the antibodies with an enzyme such as pepsin.

Additionally, chimeric, humanized, and single-chain antibodies to the polypeptides of the present invention, comprising both human and nonhuman portions, may be produced using standard recombinant DNA techniques and/or a recombinant combinatorial immunoglobulin library. Humanized antibodies may also be produced using transgenic mice which are incapable of expressing endogenous immunoglobulin heavy and light chain genes, but which can express human heavy and light chain genes. For example, human monoclonal antibodies (mAbs) directed against, e.g., a citrullinated 14-3-3 protein or fragment thereof, may be generated using transgenic mice carrying the human immunoglobulin genes rather than murine immunoglobulin genes. Splenocytes from these transgenic mice immunized with the antigen of interest may then be used to produce hybridomas that secrete human mAbs with specific affinities for epitopes from a human protein.

Chimeric antibodies, including chimeric immunoglobulin chains, may be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted.

An antibody or an immunoglobulin chain may be humanized by methods known in the art. Humanized antibodies, including humanized immunoglobulin chains, may be generated by replacing sequences of the Fv variable region that are not directly involved in antigen binding with equivalent sequences from human Fv variable regions. General methods for generating humanized antibodies are provided by Morrison (1985) Science 229:1202-07; Oi et al. (1986) BioTechniques 4:214; Queen et al., U.S. Pat. Nos. 5,585,089; 5,693,761; 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid sequences are well known to those skilled in the art and, for example, may be obtained from a hybridoma producing an antibody against a predetermined target. The recombinant DNA encoding the humanized antibody, or fragment thereof, then can be cloned into an appropriate expression vector.

Humanized or CDR-grafted antibody molecules or immunoglobulins may be produced by CDR grafting or CDR substitution, wherein one, two, or all CDRs of an immunoglobulin chain can be replaced. See, e.g., U.S. Pat. No. 5,225,539; Jones et al. (1986) Nature 321:552-25; Verhoeyan et al. (1988) Science 239:1534; Beidler et al. (1988) J. Immunol. 141:4053-60; Winter, U.S. Pat. No. 5,225,539, the contents of all of which are hereby incorporated by reference. Winter describes a CDR-grafting method that may be used to prepare the humanized antibodies of the present invention (UK Patent Application GB 2188638A; Winter, U.S. Pat. No. 5,225,539), the contents of which are hereby incorporated by reference. All of the CDRs of a particular human antibody may be replaced with at least a portion of a nonhuman CDR, or only some of the CDRs may be replaced with nonhuman CDRs. It is only necessary to replace the number of CDRs required for binding of the humanized antibody to a predetermined antigen.

Human antibodies may additionally be produced using transgenic nonhuman animals that are modified so as to produce fully human antibodies rather than the animal's endogenous antibodies in response to challenge by an antigen. See, e.g., PCT publication WO 94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the XENOMOUSE™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Monoclonal, chimeric and humanized antibodies that have been modified by, e.g., deleting, adding, or substituting other portions of the antibody, e.g., the constant region, are also within the scope of the invention. As nonlimiting examples, an antibody can be modified by deleting the constant region, by replacing the constant region with another constant region, e.g., a constant region meant to increase half-life, stability, or affinity of the antibody, or a constant region from another species or antibody class, and by modifying one or more amino acids in the constant region to alter, for example, the number of glycosylation sites, effector cell function, Fc receptor (FcR) binding, complement fixation, etc.

Methods for altering an antibody constant region are known in the art. Antibodies with altered function, e.g., altered affinity for an effector ligand, such as FcR on a cell, or the C1 component of complement, can be produced by replacing at least one amino acid residue in the constant portion of the antibody with a different residue (see, e.g., EP 388,151 A1, U.S. Pat. No. 5,624,821 and U.S. Pat. No. 5,648,260, the contents of all of which are hereby incorporated by reference). Similar types of alterations to the murine (or other species) immunoglobulin may be applied to reduce or eliminate these functions, and are known in the art.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or an aromatic nonpolar residue such as phenylalanine, tyrosine, tryptophan or alanine (see, e.g., U.S. Pat. No. 5,624,821).

Diagnostic, Prognostic and Therapeutic Methods, and Treatment Monitoring

In one aspect, the invention provides methods for diagnosing diseases and conditions that involve autoantibodies against citrullinated 14-3-3. In general, the presence or absence of an rheumatoid arthritis, or patient prognosis, may be determined by (a) contacting a biological sample obtained from a mammalian subject with at least one citrullinated 14-3-3 protein or fragment thereof; (b) detecting in the sample the level of autoantibodies that specifically bind to the citrullinated 14-3-3 protein or fragment thereof; and (c) comparing the level in such antibodies with an appropriate control, e.g., the level of native or non-citrullinated 14-3-3 protein.

The methods comprise using at least one citrullinated 14-3-3 protein or fragment thereof to detect autoantibodies against the protein. There are a variety of assay formats known to those of ordinary skill in the art for using a protein to detect antibodies in a sample. See, e.g., Harlow and Lane, Antibodies: A Laboratory Manual, Cold Spring Harbor Laboratory, 1988. As nonlimiting examples, detection of autoantibodies against citrullinated 14-3-3 may be performed using well-known methods or assays, e.g. immunoprecipitation, ELISA, Western blot analysis, immunohistochemistry, immunofluorescence, "sandwich" immunoassays, immunoradiometric assays, gel diffusion precipitation reactions, immunodiffusion assays, in situ immunoassays, precipitation reactions, agglutination assays, complement fixation assays, protein A assays, Immunoelectrophoresis assays, fluorescence activated cell sorting (FACS) analysis, radioimmunoassay, a strip test, a point of care test, and the like. The ordinarily skilled artisan will recognize that these methods may also be used to measure the level of autoantibodies against, or immune complexes with, citrullinated 14-3-3 proteins in the biological sample.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to arthritic conditions is utilized, including citrullinated 14-3-3 proteins.

In one embodiment, the assays involve the use of at least one citrullinated 14-3-3 protein or a fragment thereof immobilized on a solid support to bind to and capture autoantibodies that specifically bind the citrullinated 14-3-3 protein(s) from the remainder of the sample. The bound autoantibodies may then be detected using a detection reagent that contains a reporter group and specifically binds to the antibody/protein complex. Such detection reagents may comprise, for example, a binding agent that specifically binds to the autoantibody such as an anti-human antibody.

The solid support may be any material known to those of ordinary skill in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The citrullinated 14-3-3 protein or fragment thereof may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antibody and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and about 1 day. In one embodiment, a microtitre plate coated with streptavidin is used in conjunction with a biotinylated citrullinated 14-3-3 protein or fragment thereof.

Covalent attachment of the citrullinated 14-3-3 protein or fragment thereof to a solid support may generally be achieved by first reacting the support with a bifunctional reagent that will react with both the support and the citrullinated 14-3-3 protein or fragment thereof. The captured autoantibody can then be detected using the non-competitive "sandwich" technique where labeled ligand for the autoantibody is exposed to the washed solid phase. Alternatively, competitive formats rely on the prior introduction of a labeled antibody to the sample so that labeled and unlabelled forms compete for binding to the solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of autoantibodies.

Autoantibodies can also be detected by solid-phase radioimmunoassay (RIA). The solid phase is exposed to the serum sample in the presence of radio-labeled antibodies that compete for binding to the immobilized ligand. In this assay, the amount of radiolabel bound to the solid phase is inversely related to the amount of autoantibodies initially present in the serum sample. After separation of the solid phase, non-specifically bound radiolabel is removed by washing, and the amount of radiolabel bound to the solid phase determined. The amount of bound radiolabel is, in turn, related to the amount of autoantibodies initially present in the sample.

In one embodiment, the assay is performed in a flow-through or strip test format, wherein the citrullinated 14-3-3 protein or fragment thereof is immobilized on a membrane, such as nitrocellulose. In the flow-through test, autoantibodies to citrullinated 14-3-3 proteins within the sample bind to the immobilized citrullinated 14-3-3 protein or fragment thereof as the sample contacts the membrane. A second, labeled binding agent then binds to the immune complex as a solution containing the second binding agent contacts the membrane. The detection of bound second binding agent may then be performed as described above. In the strip test format, one end of the membrane to which citrullinated 14-3-3 protein or fragment thereof is bound is immersed in a solution containing the sample. The sample migrates along the membrane through a region containing second binding agent, e.g., to the autoantibodies, and to the area of immobilized citrullinated 14-3-3 protein or fragment thereof. Concentration of second binding agent at the area of immobilized citrullinated 14-3-3 protein or fragment thereof indicates the presence of an arthritic condition, or patient prognosis, etc. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of the autoantibody that would be sufficient to generate a positive signal in the assay, in the format discussed above. Preferred binding agents for use in such assays are citrullinated 14-3-3 proteins and fragments thereof. Such tests can typically be performed with a very small amount of biological sample and at the point of care, which may also be quantifiable.

In addition to detecting the presence of autoantibodies in a sample, many methods can be used to quantitatively measure the levels of the autoantibodies. In some methods, the antigen reacts with the autoantibody in a liquid phase, and the autoantibodies are quantitatively measured by an immunoprecipitation technique. For example, a citrullinated 14-3-3 protein or fragment thereof (i.e., full length isomer or antigenic fragments) can be detectably labeled (e.g., with an isotope or an enzyme). The polypeptides can be labeled during synthesis (e.g., by adding 35S-methionine to an in vitro translation system or cellular expression system) or after synthesis. The detectable antigen is added directly to a liquid biological sample (e.g., a serum) to form immune complexes. The immune complexes can be precipitated with polyethylene glycol. The immune complexes can also be isolated with a secondary antibody (e.g., goat anti-human immunoglobulin) or other kind of binding molecules (e.g., protein A or protein G) that is bound to a solid support (e.g., agarose or sepharose beads). The immunoprecipitates are washed several times after being separated from the liquid sample and examined for intensity of the detectable label (e.g., radioactivity). Any autoantibody present in the sample can thus be detected and quantified. Optionally, an unlabelled polypeptide can also be added to compete with the labeled polypeptide for binding to autoantibodies.

The diagnostic methods of the present invention are also directed to detecting in a subject circulating immune complexes formed between citrullinated 14-3-3 proteins and an autoantibody. The methods discussed above can be readily modified for detection of such immune complexes. For example, an immobilized binding molecule (e.g., protein A or protein G bound to a bead) can be added to a liquid biological sample. After separation from the liquid phase, immune complexes captured by the binding molecules can be analyzed with SDS-PAGE and probed with various antibodies against citrullinated 14-3-3 proteins. The captured antigens can also be subject to direct amino acid sequence analysis. Identity of the immune complexes can thus be revealed. A number of assays are routinely practiced to detect circulating immune complexes in a subject, e.g., as described in Tomimori-Yamashita et al., Lepr Rev, 70(3): 261-71, 1999 (antibody-based enzyme-linked immunosorbent assay); Krapf et al., J Clin Lab Immunol, 21(4):183-7, 1986 (fluorescence linked immunosorbent assay); Kazeem et al., East Afr Med J, 67(6):396-403, 1990 (laser immunonephelometry); and Rodrick et al., J Clin Lab Immunol, 7(3):193-8, 1982 (Protein A-glass fiber filter assay, PA-GFF, and polyethylene glycol solubilization assay).

To improve clinical sensitivity, multiple markers may be assayed within a given sample. In particular, one or more other markers of arthritis, or prognostic indicators, etc., may be assayed in combination with autoantibodies to citrullinated 14-3-3 protein. These other markers may be proteins or nucleic acids. In a preferred embodiment, one or more of the other markers are MMP proteins or nucleic acids or other factors which are commonly used as indicators for arthritis, e.g., anti-CCP, anti-RF, CRP, SAA, IL-6, SIOO, osteopontin, RF, MMP-1, MMP-3, hyaluronic acid, sCD14, angiogenesis markers and products of bone, cartilage or synovium metabolism (e.g., CTX-I and CTX-II), etc. Methods for isolating and assaying nucleic acids based on reference sequences are well known in the art, as are methods for detecting proteins of interest within a patient sample.

An ordinarily skilled artisan will recognize that each of these well known assays can be employed to detect circulating immune complexes in a biological sample for the methods of the present invention. Similarly, each of these well known assays can be employed using the antibodies to citrullinated 14-3-3 protein (and fragments thereof) disclosed in this invention to monitor the citrullination status of a 14-3-3 protein in a biological sample, e.g., determine how much how much of the 14-3-3 protein is citrullinated and/or which and how many sites of the 14-3-3 protein is citrullinated, as part of a clinical testing procedure, e.g., in diagnostic, prognostic and theranostic assays as described herein. An ordinarily skilled artisan will readily recognize how to adapt each of the assay formats, diagnostic, prognostic and theranostic assays, and kits to use the antibodies to citrullinated 14-3-3 protein as described herein to determine the citrullination status of 14-3-3 protein in a biological sample.

Combination assays may be done concurrently or sequentially. The selection of markers may be based on routine experiments to determine combinations that results in optimal sensitivity.

In one embodiment, the invention provides methods for diagnosing arthritic conditions. In general, arthritic conditions may be detected in a patient based on the presence of autoantibodies to citrullinated 14-3-3 in the synovial fluid, synovial joint, blood, plasma, or serum of a patient. In other words, autoantibodies to citrullinated 14-3-3 protein may be used as a marker to indicate arthritic conditions.

In a preferred embodiment, the invention provides methods for diagnosing rheumatoid arthritis. In general, rheumatoid arthritis may be detected in a patient based on the presence of autoantibodies to citrullinated 14-3-3 in the synovial fluid, synovial joint, blood, plasma, or serum of a patient. In other words, autoantibodies to citrullinated 14-3-3 protein may be used as a marker to indicated rheumatoid arthritis. In a particularly preferred embodiment, the citrullinated 14-3-3 protein is 14-3-3 eta.

In addition, the presence of autoantibodies to citrullinated 14-3-3, or the relative levels of autoantibodies to citrullinated 14-3-3, as determined through the use of a citrullinated 14-3-3 protein or fragment thereof may be a prognostic indicator of early-stage rheumatoid arthritis, before it progresses to a debilitating form. An advantage of early prognosis or diagnosis is earlier implementation of a treatment regimen.

To determine the presence or absence of rheumatoid arthritis in a subject, the level of autoantibodies against, or immune complexes with, citrullinated 14-3-3 in a biological sample from the subject may generally be compared to a level of autoantibodies/immune complexes corresponding to a normal control. In one preferred embodiment, the normal control is established from the average mean level of autoantibodies against, or immune complexes with, citrullinated 14-3-3 in samples from patients without rheumatoid arthritis. In an alternative embodiment, the normal control value may be determined using a Receiver Operator Curve, for example see the method of Sackett et al., Clinical Epidemiology: A Basic Science for Clinical Medicine, Little Brown and Co., 1985, p. 106-7. Briefly, in this embodiment, the control value may be determined from a plot of pairs of true positive rates (i.e., sensitivity) and false positive rates (100%-specificity) that correspond to each possible cut-off value for the diagnostic test result. The control value on the plot that is the closest to the upper left-hand corner (i.e., the value that encloses the largest area) provides the most accurate value, and a sample generating a signal that is higher than the value determined by this method may be considered positive. Alternatively, the control value may be shifted to the left along the plot, to minimize the false positive rate, or to the right, to minimize the false negative rate. In general, a sample generating a signal that is higher than the control value determined by this method is considered positive for arthritis.

In one aspect, the invention provides methods for differentiating between subtypes of arthritis. In one embodiment, the methods involve determining the level of autoantibodies against, or immune complexes with, at least one citrullinated 14-3-3 protein or fragment thereof. In a preferred embodiment, the level of autoantibodies/immune complexes to citrullinated 14-3-3 in the patient is compared to that of samples from subjects whose subtype of arthritis is known and/or previously-established.

In one aspect, the invention provides methods for determining the response potential of a patient to treatment directed at rheumatoid arthritis. In one embodiment, the methods involve determining the level of autoantibodies against, or immune complexes with, at least one citrullinated 14-3-3 protein or fragment thereof in a patient sample. In a preferred embodiment, the level of autoantibodies to/immune complexes with citrullinated 14-3-3 in the patient sample is compared to that of samples from subjects whose ability to respond to treatment is known. A relatively high level of autoantibodies to/immune complexes with citrullinated 14-3-3 in a first patient sample as compared to a sample from a non-inflammatory subject and/or a sample from another inflammatory patient may indicate the first patient is a preferred candidate for a well-known treatment, e.g., disease-modifying anti-rheumatic drug (DMARD) therapy such as anti-TNF, methotrexate, minocycline, hydroxychloroquine, sulphasalazine, azathiprine, anti-IL-1, anti-IL-6r, and the like. Conversely, a relatively low level of autoantibodies/immune complexes to citrullinated 14-3-3 in a first patient sample as compared to a sample from another inflammatory patient may indicate the first patient is not a preferred candidate for a well-known treatment, especially if the level is closer to that of a sample from a non-inflammatory subject.

Treatment regimens for various types of arthritis are known in the art. For example, a patient diagnosed with rheumatoid arthritis may be prescribed non-steroidal anti-inflammatory medications (NSAIDs) initially, to ease the discomfort and reduce the inflammation. Other treatment regimens may include, for example, steroidal anti-inflammatory medications (SAIDs e.g. Cortisol, prednisone), cyclooxygenase 2 specific inhibitors (CSIs), glucocorticoids, and/or standard disease-modifying antirheumatic drugs (DMARDs) such as, e.g., anti-TNF-alpha neutralizing agents, immunosuppressive drugs (e.g., cyclosporine, azathioprine, cyclophosphamide), antibiotics, antimalarials and cytotoxic drugs (e.g., methotrexate, sulfasalazine, leflunomide,). Treatment regimens may also advantageously include those that target citrullinated 14-3-3 proteins directly, see, e.g., PCT/CA2008/002154. Details on dosage or examples of particular drugs will be known to those of skill in the art, and may be found in, for example Harrison's Principles of Internal Medicine 15th ed. BRAUNWALD et al eds. McGraw-Hill or "The Pharmacological basis of therapeutics", 10th edition. 5 HARDMAN HG., LIMBIRD LE. editors. McGraw-Hill, New York, and in "Clinical Oncology", 3rd edition. Churchill Livingstone/Elsevier Press, 2004. ABELOFF, MD. editor.

In one aspect, the invention provides methods for monitoring treatment of rheumatoid arthritis. In one embodiment, the methods involve determining the level of autoantibodies against, or immune complexes with, at least one citrullinated 14-3-3 protein or fragment thereof in patient samples and monitoring the level of autoantibodies to/immune complexes with citrullinated 14-3-3 in a patient undergoing treatment.

The presence or relative levels of autoantibodies to/immune complexes with citrullinated 14-3-3 may correlate with the presence or relative levels of other proteins known to be associated with arthritic conditions in patients. Non-limiting examples of proteins well-known to be associated with an arthritic condition include inflammatory cytokines, such as tumor necrosis factor, and matrix metalloproteinases (MMPs), such as MMP-1 or MMP-3, etc. At least 25 different MMPs have been identified. Detection of autoantibodies to citrullinated 14-3-3 in combination with detection of at least one inflammatory cytokine and/or MMP in a patient sample may be used to diagnose arthritis. Additionally, the presence or relative levels of autoantibodies/immune complexes to citrullinated 14-3-3 in combination with at least one MMP and/or at least one inflammatory cytokine in a patient sample may be used as a prognostic indicator of early-stage arthritis, before the arthritis progresses to a debilitating form.

Also described herein are kits for evaluating an arthritic condition, and in particular, rheumatoid arthritis. Such kits typically comprise two or more components necessary for performing a diagnostic, prognostic and/or theranostic assay. Components may be compounds, reagents, containers, instructions and/or equipment. For example, one container within a kit may contain one or more citrullinated 14-3-3 protein(s) or fragment(s) thereof. Such kits may also contain a detection reagent as described above that contains a reporter group suitable for direct or indirect detection of antibody binding.

Accordingly, described herein are kits for detecting the presence of autoantibodies to/immune complexes with citrullinated 14-3-3 and optionally other markers, e.g., MMPs, in a patient sample, the kit being useful for providing a diagnostic or prognostic result suitable for diagnosing or differentiating various arthritic conditions, and more preferably, rheumatoid arthritis. Additional indications where the presence of citrullinated 14-3-3 proteins and/or autoantibodies may be implicated also include, for example, cardiovascular and/or neurodegenerative disorders. A kit may comprise at least one citrullinated 14-3-3 protein or fragment thereof, which may optionally be detectably labeled, e.g., with a radioactive label, a luminescent label, a fluorescent label, an enzyme, etc. Methods for detectably labeling proteins are well-known in the art. Such a kit may further include detection reagents specific for other markers of arthritis e.g., anti-CCP, anti-RF, CRP, SAA, IL-6, S100, osteopontin, RF, MMP-I, MMP-3, hyaluronic acid, sCD14, angiogenesis markers and products of bone, cartilage or synovium metabolism (e.g., CTX-I and CTX-II), etc. The kit may further include secondary reagents necessary for the detection of autoantibodies to citrullinated 14-3-3 immunologically, such as labeled secondary antibodies (e.g. anti-human antibodies), chromogenic or fluourogenic reagents, polymerization agents and the like. Instructions for using the kit for diagnostic or prognostic purposes, including appropriate comparison standards for quantifying and/or evaluating the level of such autoantibodies in the context of a particular disease state, may also be advantageously provided in printed form and/or recorded on a suitable media.

EXAMPLES

As 14-3-3η is liberated into the synovial space in RA where PAD enzymes are present, we investigated whether 14-3-3η is a citrullination target that may be used in the diagnosis of RA, and if so, whether citrullinated 14-3-3η or fragments could be used to identify anti-CCP negative RA patients. Identification of citrullination sites on 14-3-3η involved a three (3) stage process 1) in silico prediction, 2) in vitro determination and 3) validation or identification with clinical specimens.

Example 1: In Silico Identification of Citrullination Sites

Ariginine (R) moieties that represent putative citrullination sites were identified based on 1) location of the "R" in relation to the native 3D protein configuration; 2) accessibility of "R" to PAD enzyme and 3) sequence flanking "R". Five (5) putative citrullination sites were identified corresponding to "R": 4, 12, 19, 61 and 227.

Example 2: In Vitro Determination of Citrullination Sites

In vitro citrullination was performed whereby recombinant human 14-3-3 eta was co-incubated with either recombinant human PAD2 or PAD4 since these two isoforms have been reported to be the two most relevant in RA.

Briefly, PAD2 (MQ16.201) and PAD4 (MQ16.203) were procured from ModiQuest Research. The enzymes were further diluted in 100 μl of PAD buffer (0.1 M Tris HCl, pH 7.4, mM CaCl2 with 5 mM DTT, 1 mM PMSF, 10 μg/ml aprotonin, 10 μg/ml leupeptin and 10 μg/ml pepstatin) bringing the stock concentrations of PAD2 to 80 mU/μl and PAD4 to 82.5 mU/μl.

Ten (10) μg of full-length recombinant 14-3-3 eta was incubated with either PAD2 (8 mU) or PAD4 (8.2 mU). The reaction mixture was adjusted to 100 μl with PAD buffer and incubated at 37° C. for 2 h. Following incubation, the reaction was terminated through the addition of 25 μl of 4× Lammelli buffer. The proteins were resolved by SDS-PAGE and the band corresponding to 14-3-3 eta was excised. The excised bands were eluted from the gel, trypsinized and then analysed using Fourier Transform Mass Spectrometry to identify determinated sites as described by others. The results yielded four putative citrullination sites with PAD2 and 3 with PAD4 for which the results are described in Table 4.

TABLE 4

| Citrullination sites for 14-3-3η as determined in vitro | | | | |
|---|---|---|---|---|
| Site | Sequence | SEQ ID NO: | No PAD | PAD2 | PAD4 |
| Position 4 | mgdReqllq | 23 | No | Yes | Yes |
| Position 19 | qaeRyddma | 24 | No | Yes | Yes |
| Position 42 | dRnllsvayk | 25 | No | Yes | Yes |
| Position 61 | sswRvissie | 26 | No | Yes | No |

Example 3: Detection of Antibodies Directed to Citrullinated 14-3-3 Eta Using Clinical Samples In vitro citrullination was performed as described in Example 2, and 96-well plates were coated with either the citrullinated or non-citrullinated form of recombinant 14-3-3 eta. The human auto-antibody response directed to either the native or citrullinated forms of 14-3-3 eta in anti-CCP positive and negative patients were quantified using an anti-human antibody.

To evaluate whether these novel autoantibodies are detectable in anti-CCP negative RA patients and differentially expressed compared to healthy controls, reactivity to both non-citrullinated and citrullinated-14-3-3 eta was measured in 30 anti-CCP negative RA patients and 30 confirmed anti-CCP negative healthy controls. Mean and median autoantibody levels expressed in units (U) was evaluated and corresponding t-tests and Mann-Whitney U-tests were used to determine differences within and between groups. The area under the ROC curve (AUC) was generated for diagnostic utility estimates and to determine likelihood ratios (LR) for various anti-citrulinated-14-3-3 eta cut-offs.

Figure 2:
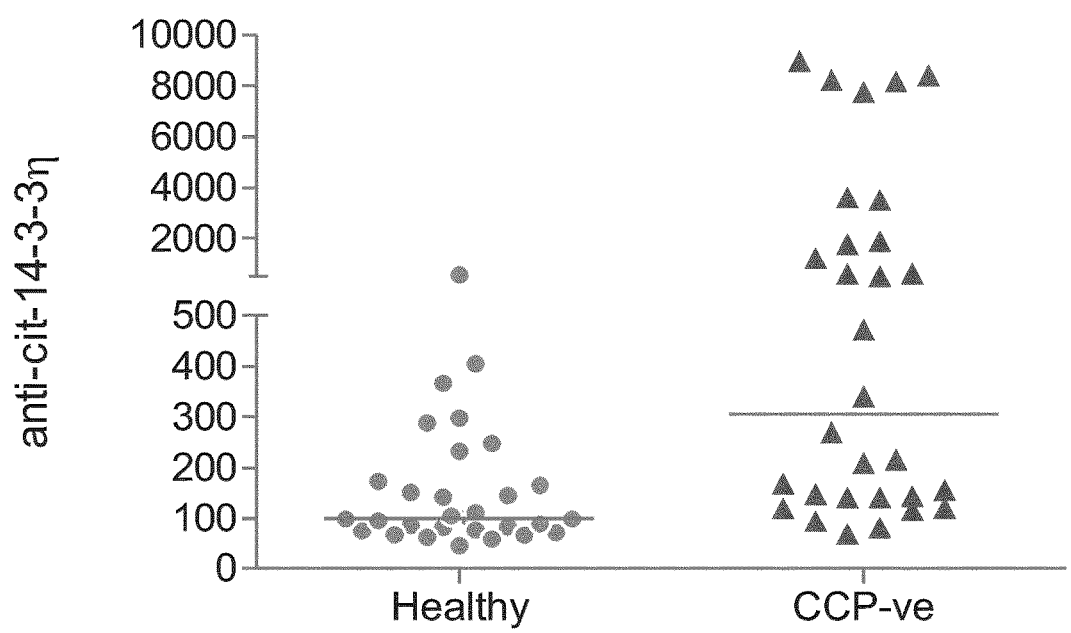
FIG. 2 is a dot plot representing the 14-3-3 eta citrullination specific autoantibody response in thirty anti-CCP negative ("CCP −ve") healthy controls (●) compared to thirty anti-CCP negative rheumatoid arthritis (RA) patients (▲). The y-axis (anti-cit-14-3-3ri) represents the autoantibody response towards the citrullinated form of the 14-3-3 eta antigen for each individual subject.

FIG. 1 shows that, compared to non-citrullinated 14-3-3 eta, up to 25× higher reactivity to citrullinated-14-3-3 eta in 2 of the 3 anti-CCP positive RA patients was observed, revealing for the first time the expression of autoantibodies to the citrullinated form of 14-3-3 eta in RA. Within the anti-CCP negative RA group, significantly higher reactivity was observed to citrullinated 14-3-3 eta compared to native 14-3-3 eta (1943U versus 395U, p=0.01). No significant differences in reactivity were observed within the healthy group. FIG. 2 shows that anti-citrullinated-14-3-3 eta antibody expression was significantly higher in anti-CCP negative RA patients with means (SD) and medians (min-max) of 1943U (3045U) and 306U (68-8982U) compared to 155U (122U) and 100U (45-564U) for healthy controls, p<0.002. The corresponding ROC AUC for anti-citrullinated-14-3-3 eta antibody differential expression in anti-CCP negative RA patients compared to healthy controls was 0.79 (95% CI 0.68-0.91; p<0.0001). At a cut-off of 320U, the specificity and sensitivity were 90% and 50% delivering an LR positive of 5 increasing to 14 at 439U with a corresponding specificity of 97% and sensitivity of 47%.

|  | Healthy N = 58 | CCP-ve RA patients N = 30 |
| --- | --- | --- |
| mean (SD) | 155 U (122 U) | 1943 U (3045 U) |
| median (min-max) | 100 U (45-564 U) | 306 U (68-8982 U) |
| AUC | | 0.79 |
| 95% CI | | 0.68-0.91 |
| P-value | | <0.0001 |
| Cut-off | | 439 U |
| LR | | 14 |
| Specificity | | 97% |
| Sensitivity | | 47% |

Example 4: Identification of Citrullination Sites Using Clinical Samples 14-3-3 eta is immunoprecipitated from clinical samples positive for the 14-3-3 eta protein and the immunoprecipitated protein is resolved by SDS-PAGE and the band corresponding to 14-3-3 eta excised. The excised bands are eluted from the gel, trypsinized and then analysed using Fourier Transform Mass Spectrometry to identify determinated sites on the protein.

Selection of clinically relevant 14-3-3 eta citrullination sites

To identify the most relevant 14-3-3 eta citrillunation sites, peptides bearing either an arginylated or a citrullinated moiety are used to screen and select the most relevant citrullination sites on 14-3-3 eta that can be used to distinguish both the non-citrullinated form of the protein as well as differentiate between healthy individuals or those affected with an arthritide.

Comparing 14-3-3 eta expression levels in clinical samples using two distinct approaches, measurement by MRM/LC-MS and ELISA, illustrates that differences in expression may be attributable to citrullination since determination of arginine yielding citrulline results in a miscleavage since trypsin does not cut when the protein is citrullinated, see Table 5. Specifically in samples 1-6 high levels of the 14-3-3 eta protein are detectable by ELISA but appear to have negligible levels when measured by mass spectrometry compared with samples 7-12. With mass spectrometry samples are trypsinized and 14-3-3 eta levels are quantified through measurement of a peak intensity as a results of a specific peptide mass, the peptide of which is "AV TELNEPLSNED" (SEQ ID NO: 27) which resides next to Arg-42 which has been described here as a citrullination site. Citrullination specific antibodies to Arg-42 will be examined by ELISA in samples 1-12 to verify that Arg-42 is a clinically relevant citrullination site.

TABLE 5

| Sample ID | Mass Spec | ELISA |
| --- | --- | --- |
| 1 | 0 | 297.8 |
| 2 | 0 | 23.85 |
| 3 | 0 | 33.11 |
| 4 | 139 | 1078.1 |
| 5 | 0 | 65.85 |
| 6 | 0 | 18.7 |
| 7 | 5679 | 64.47 |
| 8 | 1283 | 29.07 |
| 9 | 9791 | 7.9 |
| 10 | 14278 | 47.7 |
| 11 | 1602 | 3.2 |
| 12 | 2451 | 31.3 |

Example 5: Diagnosis, Prognosis, and/or Treatment Monitoring

Detection of Autoantibodies to Citrullinated 14-3-3 Eta Protein in a Clinical Sample The data presented in FIG. 1 demonstrates that detection of autoantibodies to the citrullinated form of full length 14-3-3 eta is useful in identifying patients whom are anti-CCP negative thus complementing the anti-CCP test in diagnosing seronegative RA patients. The differential expression in RA versus healthy individuals presented in FIG. 2 demonstrates that anti-citrullinated 14-3-3 eta autoantibodies are higher in RA patients and will likely be highly specific for RA. Citrullinated 14-3-3 eta fragments, each harboring the different citrullinated sites, will be also be used to detect autoantibodies to each of the different sites. Such detection for site specific autoantibodies is likely be as or more specific for RA than the full-length citrullinated 14-3-3 eta protein.

Determination of the Citrullination Status of a 14-3-3 Protein in a Clinical Sample If a patient measures positive for autoantibodies to citrullinated 14-3-3 eta protein, the protein's citrullination status will be evaluated using monoclonal antibodies raised against either or both full-length citrullinated 14-3-3 eta protein or citrullinated fragments thereof to evaluate two parameters:
1) How much of the protein is citrullinated?
2) What sites on protein are citrullinated and/or how many sites are citrullinated?

Titres of the citrullinated 14-3-3 eta auto-antibodies will be examined on their own and in relation to the 14-3-3 eta serum protein levels as well as the citrullination status of the protein. Table 5 below defines possible outcomes.

TABLE 5

| anti-citrullinated 14-3-3 eta auto-antibodies levels | 14-3-3 eta protein levels | Prognosis |
|---|---|---|
| High | High | Bad |
|  | Low | Good |
| Low | High | Bad |
|  | Low | Good or 14-3-3 eta is not central to disease process |

For therapy response and monitoring, high levels of anti-citrullinated 14-3-3 eta autoantibodies may implicate use of certain therapies over others. Additionally, it is expected that a higher % of the protein being citrullinated is correlated with a more significant disease burden. It is also expected that different citrullination sites may impart different biological activity on the protein and thus associate with different clinical outcomes. This information may then be used to assists in determining the type of therapy that would be best for a particular patient and for monitoring therapy response.

For instance, high titres and/or high citrullination status would be useful for treatment using B-cell inhibitors like rituximab or inhibitors that directly target peptidyl arginine deminiases. Monitoring outcomes by measuring pre- and post-treatment levels may also be useful. For instance if levels decrease, then patient may be receiving a benefit from drug i.e. respond to therapy whereas if the levels remain unchanged or increase, then the therapeutic dose may need to be increase or the class of therapy may need to be switched.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for diagnosing Rheumatoid Arthritis in a subject comprising:
   i) obtaining a biological sample from a subject suspected of having or at risk for developing Rheumatoid Arthritis,
   ii) contacting said biological sample from the subject with at least one citrullinated 14-3-3 eta protein or fragment thereof comprising at least one citrullinated 14-3-3 eta epitope under a condition suitable for the formation of at least one immune complex between the citrullinated 14-3-3 eta protein or fragment thereof and autoantibodies specific for said citrullinated 14-3-3 eta epitope that may be present in the biological sample, wherein said citrullinated 14-3-3 eta epitope comprises a citrulline residue at a position selected from the group consisting of position 4, position 12, position 19, position 42, position 61, position 86 and position 227 of SEQ ID NO: 5; and
   iii) detecting the presence of immune complexes between the citrullinated 14-3-3 eta protein or fragment thereof and autoantibodies that specifically bind the citrullinated 14-3-3 eta epitope of the citrullinated 14-3-3 eta protein or fragment thereof, wherein said presence of said immune complexes is indicative of Rheumatoid Arthritis in said subject.

2. The method of claim 1, wherein said detecting step further comprises measuring the amount of autoantibodies against the citrullinated 14-3-3 eta protein or fragment thereof.

3. The method according to claim 1, wherein the citrullinated 14-3-3 eta protein or fragment thereof is detectably labeled with a label selected from the group consisting of a radioactive label, a luminescent label, and a fluorescent label, and an enzyme.

4. The method according to claim 1, wherein the citrullinated 14-3-3 eta protein or fragment thereof is bound to a solid support.

5. The method according to claim 1, wherein the autoantibodies are detected by an ELISA assay.

6. The method according to claim 1, wherein said detection occurs by chemiluminescence.

* * * * *